(12) United States Patent
Harr et al.

(10) Patent No.: US 9,114,243 B2
(45) Date of Patent: Aug. 25, 2015

(54) MANUAL VALVE ACTUATOR FOR MEDICAL FLUID DELIVERY SET

(75) Inventors: James M. Harr, Foristell, MO (US); Kenneth M. Breitweiser, Brighton, IL (US)

(73) Assignee: Covidien LP, Mansfield, MA (US)

( * ) Notice: Subject to any disclaimer, the term of this patent is extended or adjusted under 35 U.S.C. 154(b) by 1164 days.

(21) Appl. No.: 12/389,119

(22) Filed: Feb. 19, 2009

(65) Prior Publication Data
US 2010/0211022 A1 Aug. 19, 2010

(51) Int. Cl.
*A61M 39/22* (2006.01)
*A61M 5/142* (2006.01)
*A61M 5/168* (2006.01)

(52) U.S. Cl.
CPC ......... *A61M 39/223* (2013.01); *A61M 5/14232* (2013.01); *A61M 5/16827* (2013.01); *A61M 5/16877* (2013.01); *A61M 5/16881* (2013.01); *A61M 2039/226* (2013.01); *A61M 2205/14* (2013.01); *A61M 2205/6018* (2013.01); *A61M 2205/6036* (2013.01); *A61M 2209/04* (2013.01)

(58) Field of Classification Search
CPC .......... A61M 5/16881; A61M 39/223; A61M 2205/14; A61M 5/16877; A61M 2205/6018; A61M 2205/6036; A61M 5/14232; A61M 2039/226; A61M 2209/04
USPC .............................. 604/32, 246, 248, 251, 256
See application file for complete search history.

(56) References Cited

U.S. PATENT DOCUMENTS

| | | | |
|---|---|---|---|
| 3,803,914 A | 4/1974 | Noiles | |
| 4,079,737 A | 3/1978 | Miller | |
| 4,294,246 A | 10/1981 | Aslanian | |
| 4,312,493 A | 1/1982 | Stauffer | |
| 4,361,147 A | 11/1982 | Aslanian | |
| 4,807,660 A | 2/1989 | Aslanian | |
| 5,318,515 A | 6/1994 | Wilk | |
| 5,649,810 A | 7/1997 | Schweitzer, Jr. et al. | |
| 6,926,706 B1 | 8/2005 | Sealfon | |
| 7,232,420 B1 | 6/2007 | Abulhaj | |
| 7,361,165 B2 | 4/2008 | Simon | |
| 7,462,170 B2 | 12/2008 | Fournie et al. | |
| 2003/0135164 A1* | 7/2003 | Simon ........................ | 604/246 |
| 2005/0267418 A1 | 12/2005 | Fournie et al. | |
| 2007/0078431 A1* | 4/2007 | Hudson et al. .............. | 604/500 |
| 2008/0149873 A1 | 6/2008 | Cimberio et al. | |

FOREIGN PATENT DOCUMENTS

WO 2006121905 A2 11/2006

OTHER PUBLICATIONS

"Mechanism". Merriam-Webster Online Dictionary. <http://www.merriam-webster.com/dictionary/mechanism>.*
European Search Report regarding related application serial No. EP 10153984.9 dated Jul. 9, 2010, 6 pgs.

* cited by examiner

*Primary Examiner* — Theodore Stigell
*Assistant Examiner* — Lauren M Peng

(57) ABSTRACT

A manual valve actuator for a medical fluid delivery set is disclosed. The manual valve actuator comprises a holder adapted to removably receive a valve mechanism of the medical fluid delivery set, a valve driver, and a handle for rotating the valve driver and thereby the valve rotor when the valve mechanism is received in the holder. Also disclosed is a method for rinsing a medical fluid delivery set utilizing the manual valve actuator.

16 Claims, 21 Drawing Sheets

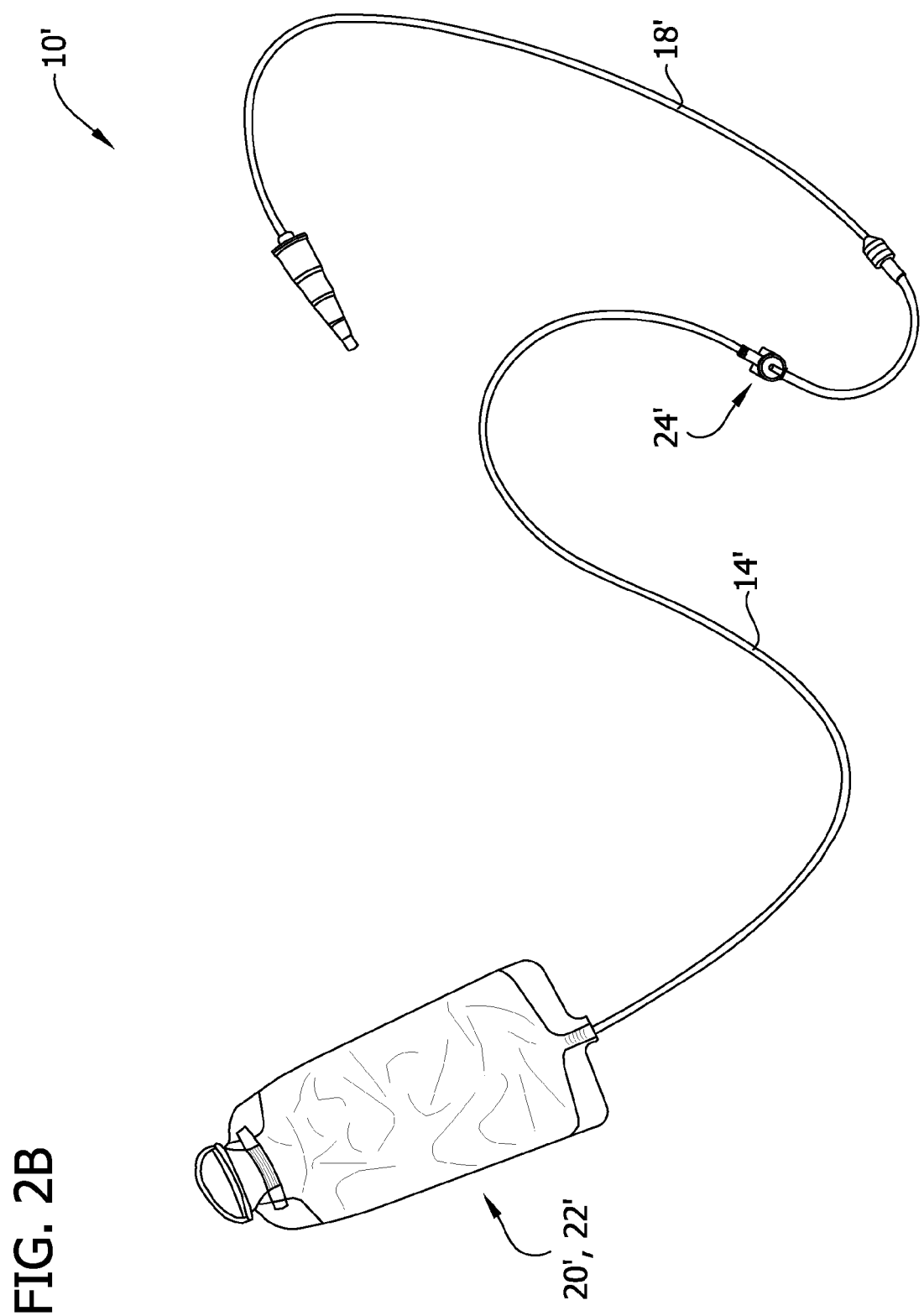

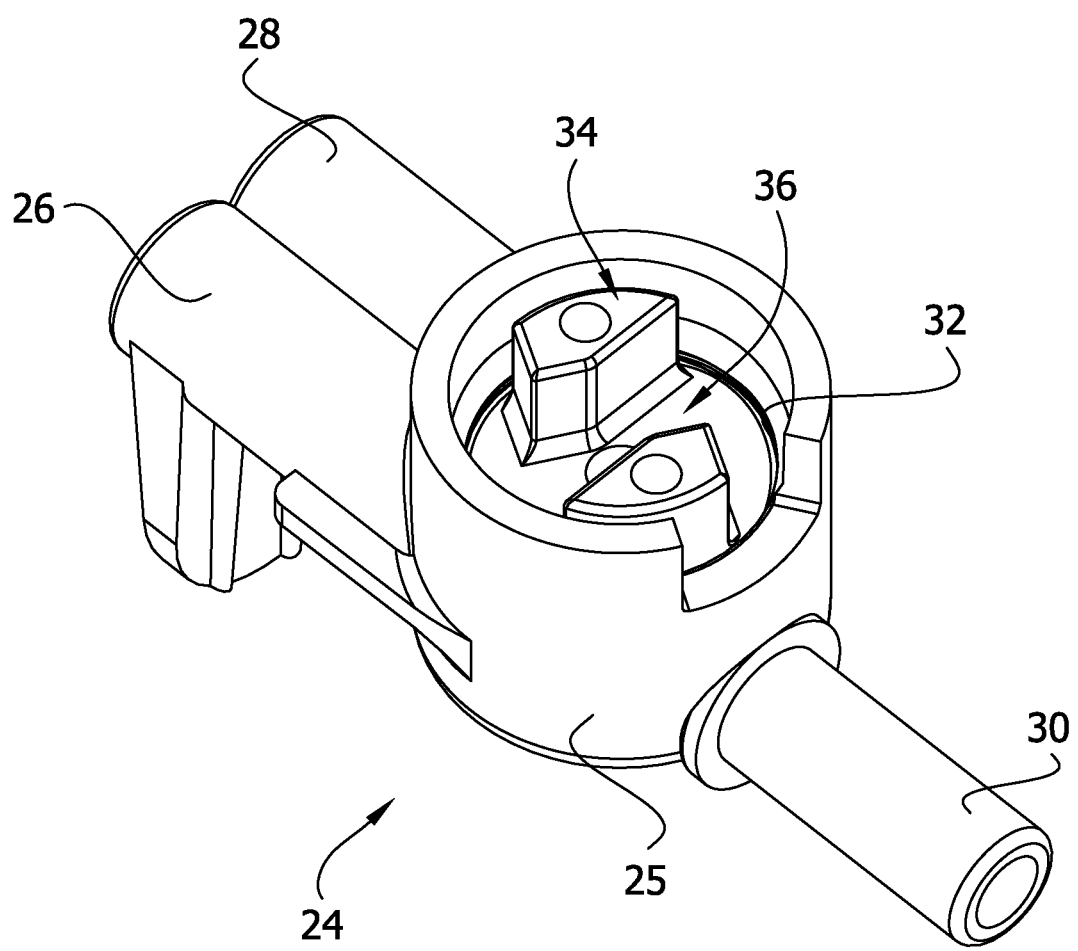

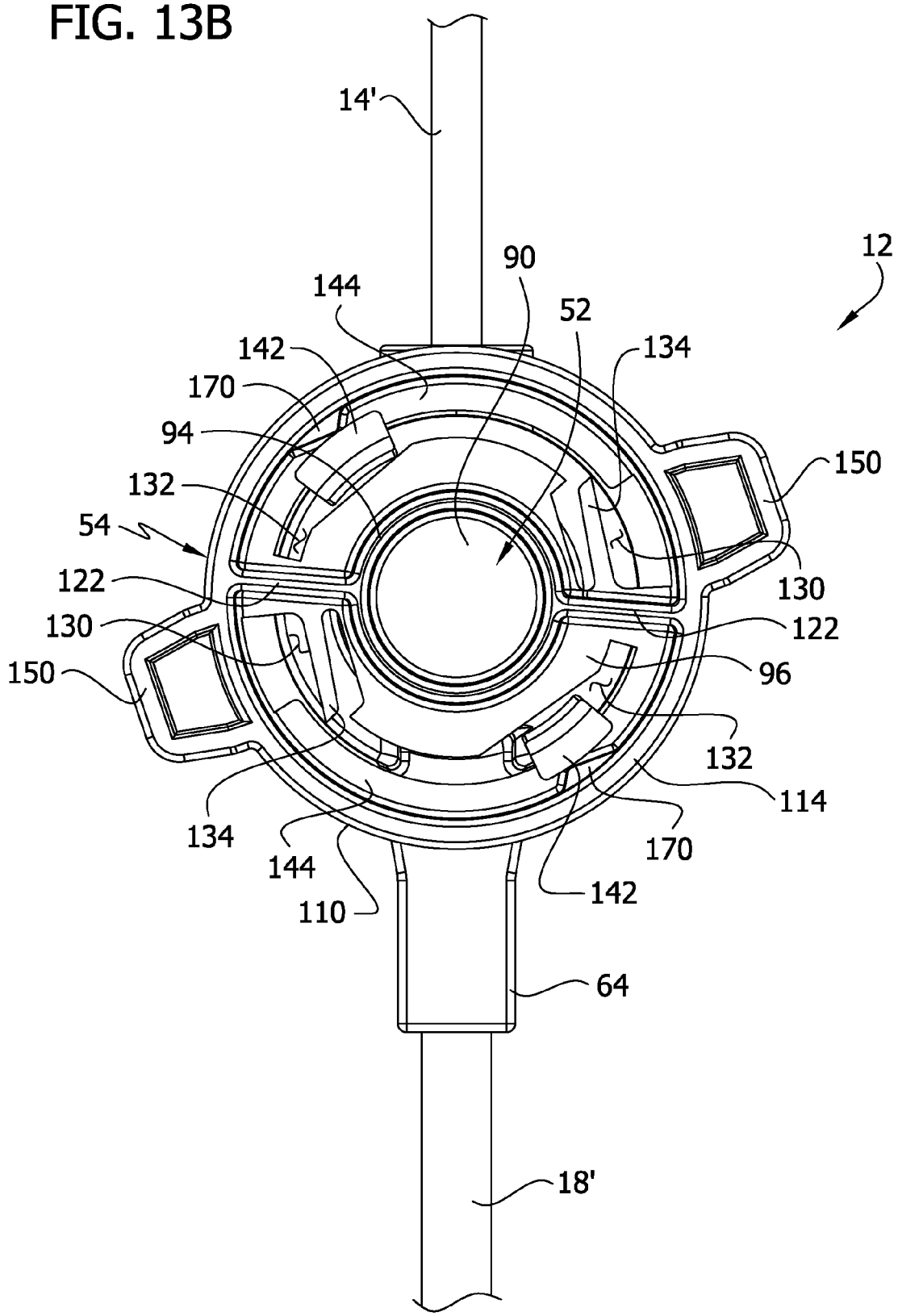

MANUAL VALVE ACTUATOR FOR MEDICAL FLUID DELIVERY SET

FIELD OF THE INVENTION

The present invention generally relates to a manual valve actuator, and more particularly to a manual valve actuator for a medical fluid delivery set.

BACKGROUND OF THE INVENTION

Administering fluids containing medicine or nutrition to a patient is well known in the art. Fluid may be administered to the patient by a medical fluid delivery set loaded on a flow control apparatus, which automatically delivers fluid at a controlled rate.

The delivery set comprises tubing that delivers fluid from a fluid source to a patient. A valve mechanism is typically located on the tubing for permitting or preventing fluid flow through the delivery set. When the delivery set is loaded on the flow control apparatus, the valve mechanism is automatically moved to alternate positions that either prevent or permit fluid flow through the tubing.

U.S. Pat. No. 7,462,170, which is assigned to Covidien A G, discloses a flow control apparatus comprising a peristaltic pump and an automatic valve controller. When a delivery set is loaded on the flow control apparatus, the peristaltic pump moves fluid through the tubing, and the valve controller automatically actuates a valve rotor of the valve mechanism to prevent or permit fluid flow though the delivery set.

The valve rotors of such valve mechanisms are typically relatively small and difficult to turn by hand. Users simply cannot impart sufficient rotational force on the rotor by hand to overcome its rotational resistance. Moreover, for safety reasons, the valve mechanisms may purposely be designed to impede users from turning the valve rotor by hand.

In certain circumstances, however, it is desirable that users have the ability to manually actuate the valve rotor to prevent or permit fluid flow through the delivery set. For example, after delivery of a medical fluid to a patient, the delivery set may require cleaning. Users may remove the delivery set from the flow control apparatus to clean the set by hand. In another example, a user may remove the delivery set from the flow control apparatus to flush a clogged tube. To actuate the valve rotor without the automatic valve controller, the user must be able to manually actuate the valve rotor. Therefore, there is a need for a manual valve actuator for a medical fluid delivery set.

SUMMARY OF THE INVENTION

In one embodiment, the present invention comprises a manual valve actuator for a medical fluid delivery set that includes a valve mechanism having a valve rotor. The manual valve actuator comprises a holder, a valve driver, and a handle. The holder is adapted to removably receive the valve mechanism and is shaped to hold the valve mechanism against rotation with respect to the holder. The valve driver is mounted for rotation with respect to the holder and is positioned with respect to the holder to operatively engage the valve rotor when the valve mechanism is received in the holder. The handle is operatively connected to the valve driver for rotating the valve driver and thereby the valve rotor when the valve mechanism is received in the holder.

In another embodiment, the present invention comprises a method of rinsing a medical fluid delivery set having a valve mechanism that includes a valve rotor and tubes extending from the valve mechanism. The method comprises inserting the valve mechanism into a holder of a manual valve actuator to a position in which a valve driver of the manual valve actuator engages the valve rotor. A handle of the manual valve actuator is then used to rotate the valve driver and thereby the valve rotor to a first selected position. The method further comprises flushing a rinsing fluid through the medical fluid delivery set with the valve mechanism in the first selected position.

In another embodiment, the present invention comprises a manual valve actuator for a medical fluid delivery set that includes a valve mechanism having a valve rotor. The manual valve actuator comprises a holder, a valve driver, and a handle. The valve driver comprises a ring and a pocket connected to the ring adapted to removably receive the valve mechanism and shaped to hold the valve mechanism against rotation with respect to the holder. The valve driver is rotatably disposed within a central opening of the ring, and the valve driver is sized and shaped for reception in a recess defined by the valve rotor. The valve driver is positioned with respect to the holder so that the valve driver engages the valve rotor in the recess when the valve mechanism is received in the holder. The handle is operatively connected to the valve driver for rotating the valve driver and thereby the valve rotor when the valve mechanism is received in the holder. The handle is annular with a central opening, and the ring of the holder is disposed within the central opening.

Other objects and features will be in part apparent and in part pointed out hereinafter.

BRIEF DESCRIPTION OF THE DRAWINGS

FIG. 2B is a perspective of a second embodiment of a medical fluid delivery set;

FIG. 4B is a perspective similar to the view of FIG. 4A but showing the valve rotor turned to an open position permitting fluid flow through the valve mechanism;

FIG. 13B is a rear elevation of the manual valve actuator and the fluid delivery set of FIG. 10B, the handle of the manual valve actuator being shown turned between the positions shown in FIGS. 10A and 10B.

Corresponding reference characters indicate corresponding parts throughout the drawings.

DESCRIPTION OF THE PREFERRED EMBODIMENTS

Figure 1:
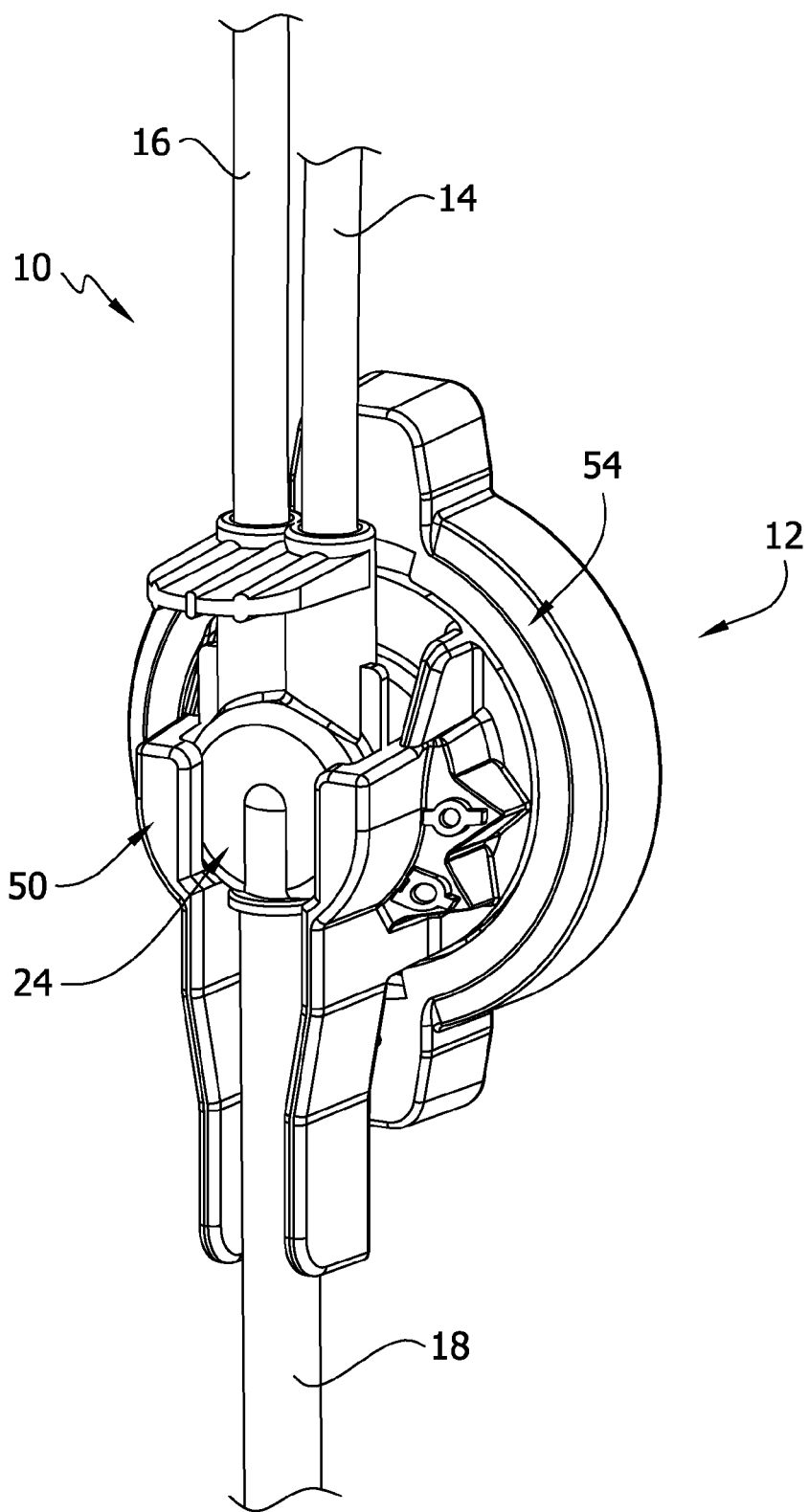
FIG. 1 is an enlarged front perspective of a medical fluid delivery set loaded on a manual valve actuator of this invention.
Figure 2A:
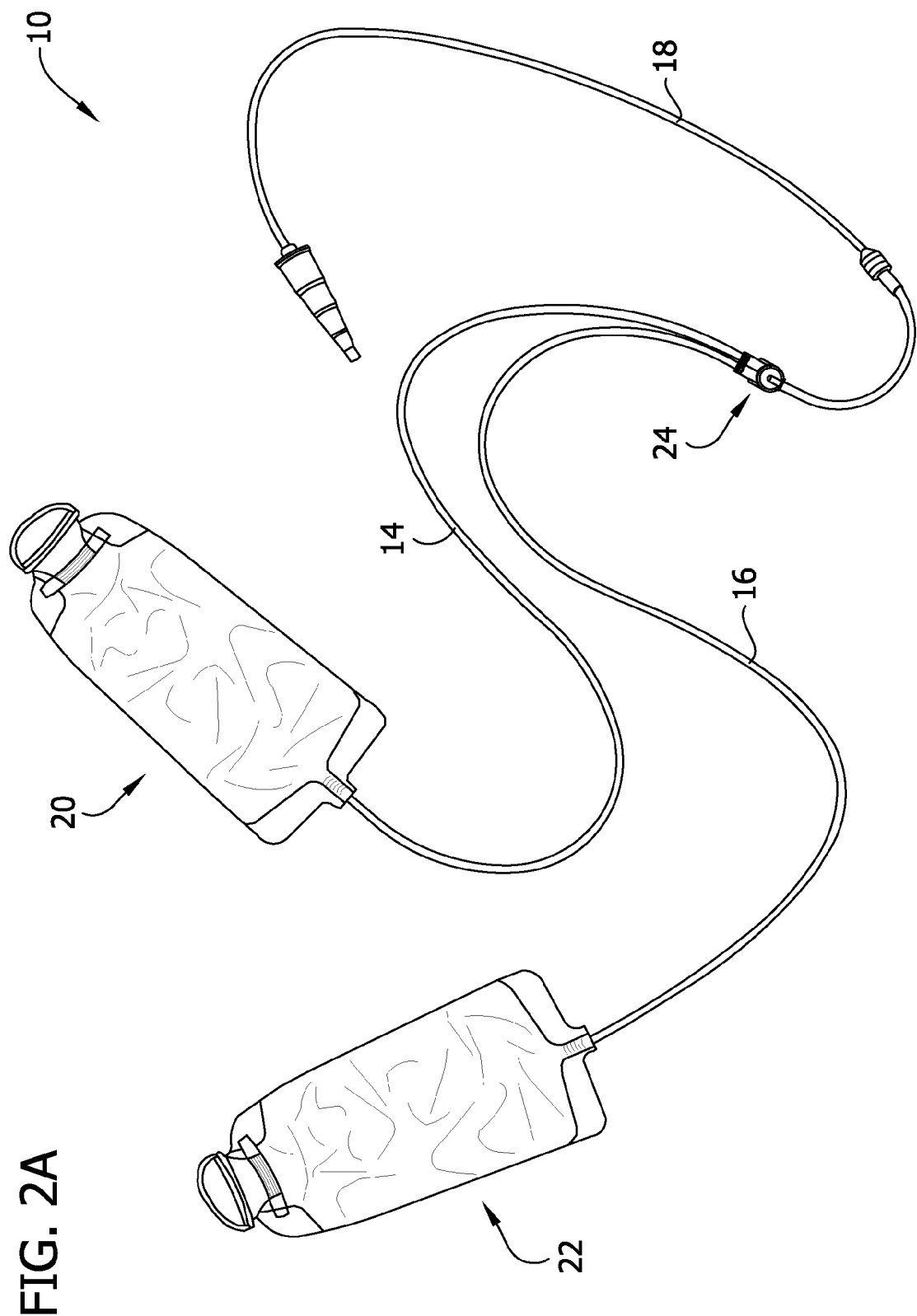
FIG. 2A is a perspective of a first embodiment of a medical fluid delivery set.

Referring to the drawings, and more particularly to FIG. 1, a medical fluid delivery set 10 is shown mounted on one embodiment of a manual valve actuator 12 of the present invention. The medical fluid delivery set 10, shown by itself in FIG. 2A, has two source tubes 14, 16 and one delivery tube 18, all of which are adapted for fluid flow therethrough. The first source tube 14 is in fluid communication with a medical fluid source 20, and the second source tube 16 is in fluid communication with a rinsing fluid source 22. A valve mechanism 24 is in fluid communication with the two source tubes 14, 16 and the delivery tube 18. As shown in FIG. 2B, a fluid delivery set 10' (corresponding parts being designated by the corresponding reference numbers, plus a prime designator (')) may comprise a single source tube 14', in which case the medical fluid source 20' and the rinsing fluid source 22' may be interchangeably placed in fluid communication with the single source tube. The delivery tube 18, 18' is generally administered to a patient for delivery of the medical fluid or positioned over a drain for disposal of flushed medical fluid and rinsing fluid.

Figure 3:
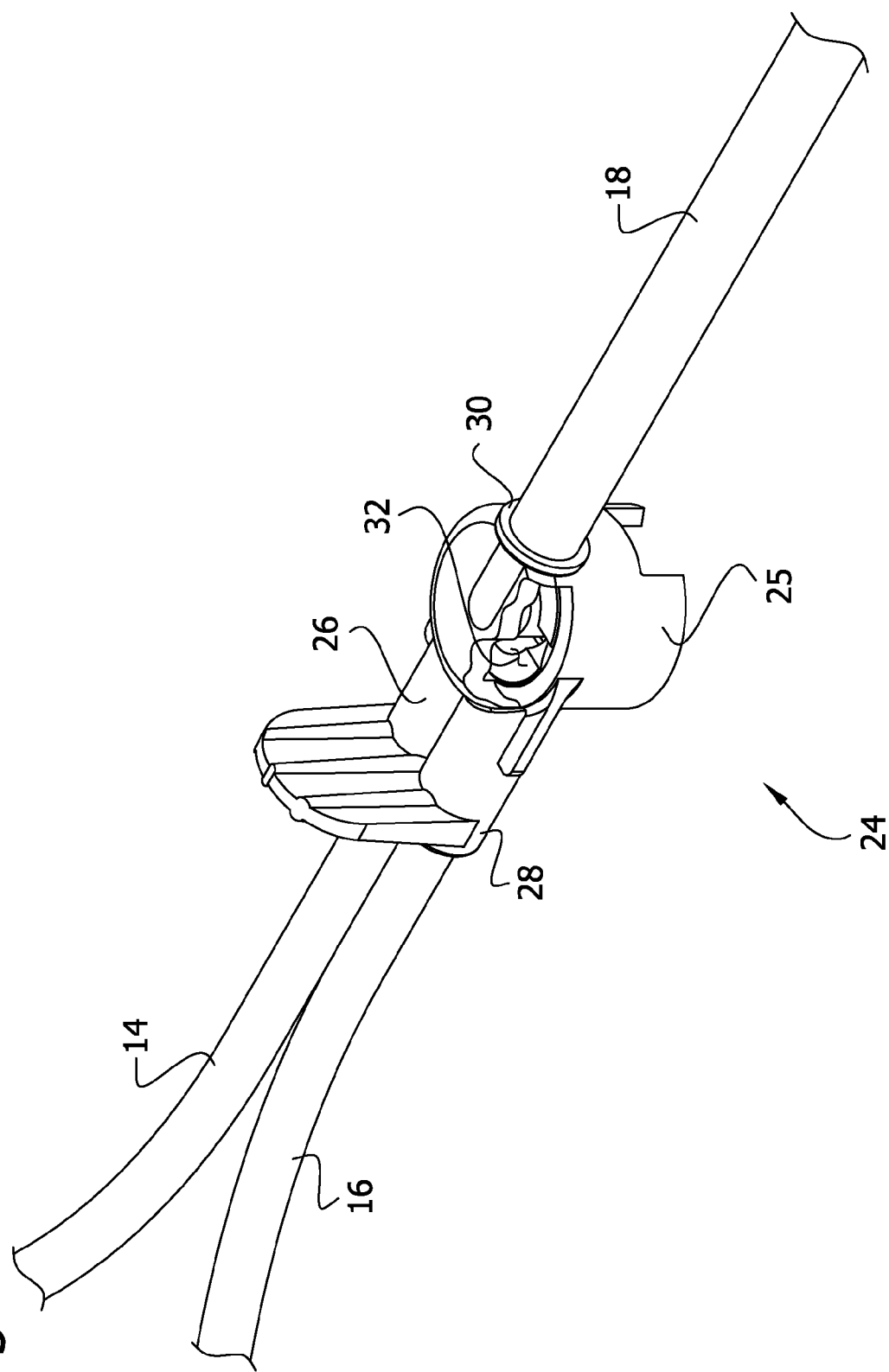
FIG. 3 is an enlarged perspective of a valve mechanism of the medical fluid delivery set of FIG. 2A, a portion of the valve mechanism being broken away.
Figure 4A:
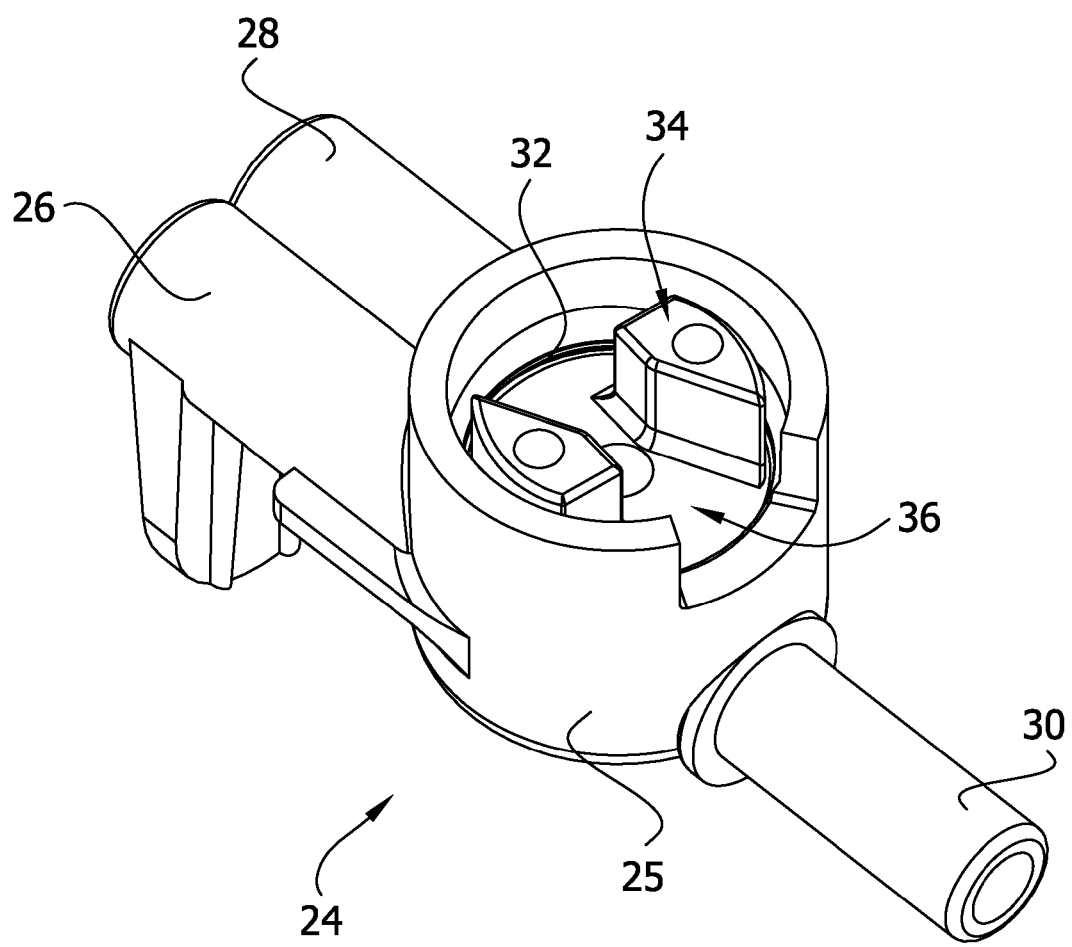
FIG. 4A is a perspective of the reverse side of the valve mechanism of FIG. 3, a valve rotor of the valve mechanism being shown turned to a closed position preventing fluid flow through the valve mechanism.

As shown in FIG. 3, the valve mechanism 24 comprises a valve housing 25 having a first inlet 26, a second inlet 28, an outlet 30, and a chamber 32. The first inlet 26 is in fluid communication with the medical fluid source 20 via the first source tube 14, and the second inlet 28 is in fluid communication with the rinsing fluid source 22 via the second source tube 16. In the delivery set 10' with only one source tube 14', the valve mechanism 24' has only one inlet. The inlets 26, 28 are in fluid communication with the outlet 30 through the chamber 32. As shown in FIGS. 4A and 4B, a valve rotor 34 is disposed in the chamber 32 and may be rotated to alternate positions to permit or prevent fluid flow through the valve mechanism. For example, FIG. 4A shows the rotor 34 turned to a closed position preventing fluid flow through the valve mechanism 24. FIG. 4B shows the rotor 34 turned to an open position permitting fluid flow through the valve mechanism 24 from the inlet 28 in fluid communication with the rinsing fluid source 22.

The valve rotor 34 is adapted to operatively engage a valve driver for actuating the valve rotor. As shown in FIGS. 4A and 4B, the outside-facing surface of the valve rotor 34 defines a slot or channel 36 that is sized and shaped to receive a valve driver so that rotation of the valve driver imparts rotation to the rotor, as described in more detail below. The valve rotor 34 may have other configurations adapted to operatively engage a valve driver.

Figure 5A:
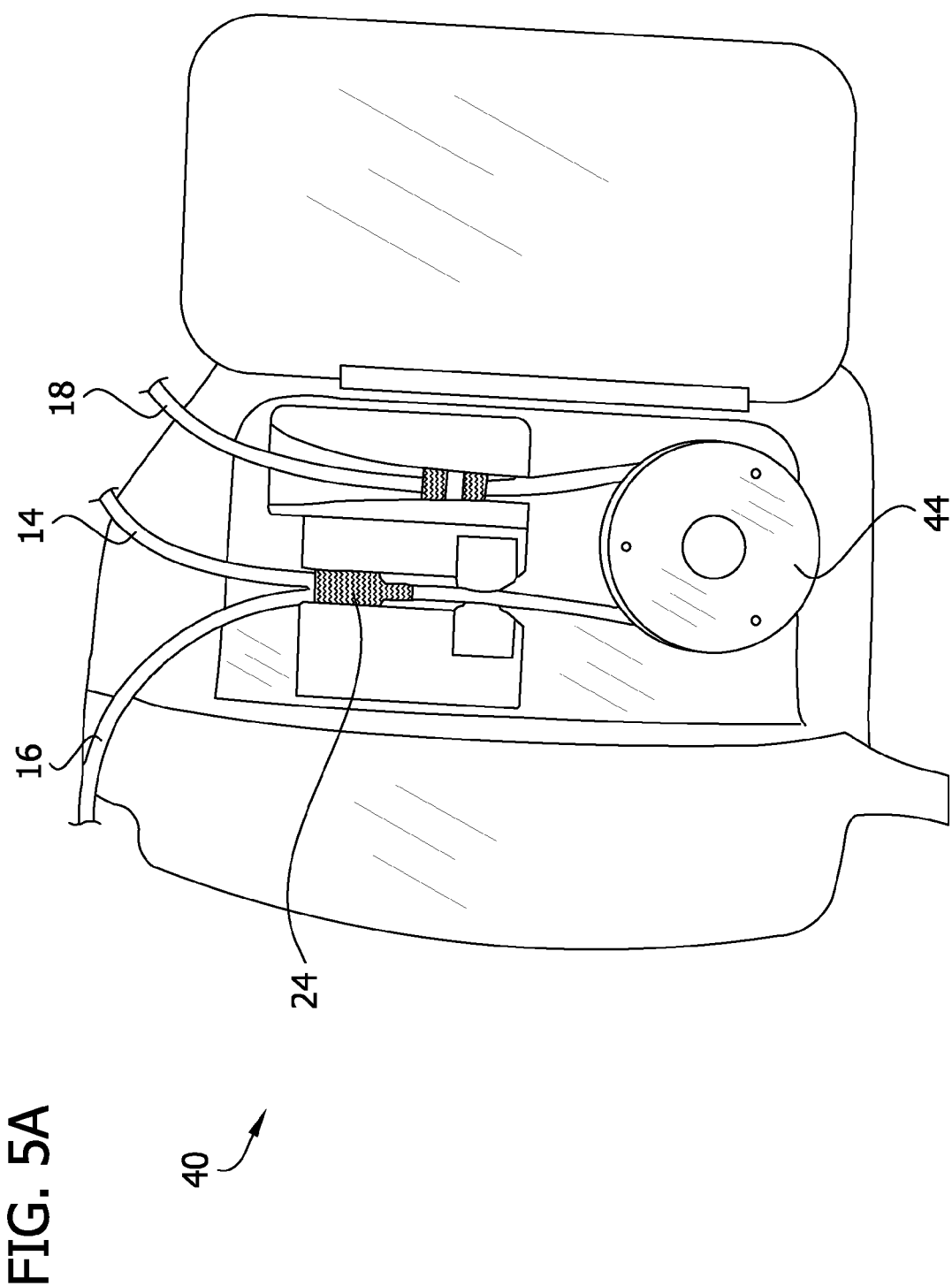
FIG. 5A is a front elevation showing the medical fluid delivery set of FIG. 2A loaded on a flow control apparatus.
Figure 5B:
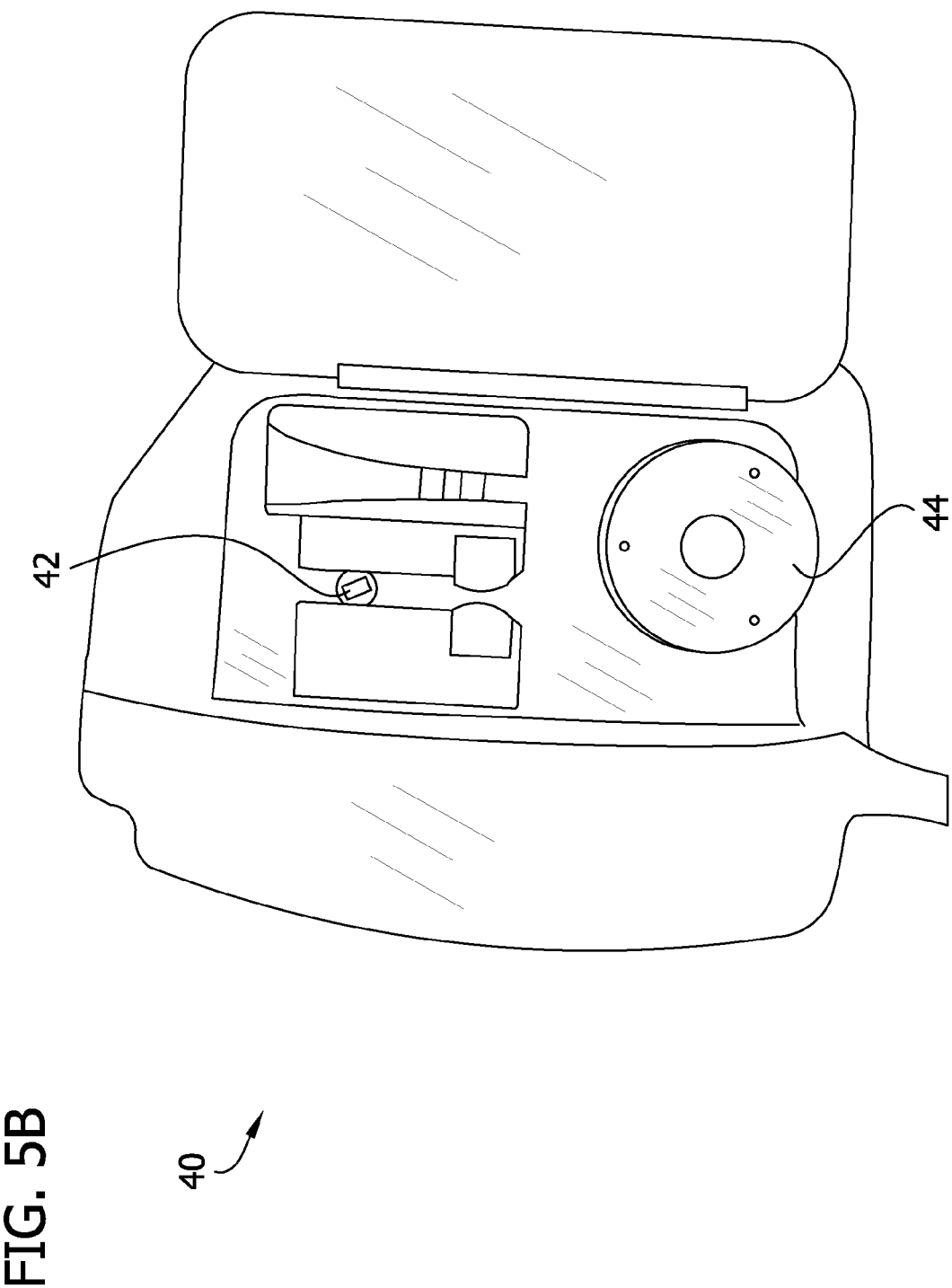
FIG. 5B is a view similar to FIG. 5A but showing the medical fluid delivery set removed from the flow control apparatus.

A medical fluid delivery set 10 as described herein is generally adapted for use with a flow control apparatus 40 to automatically deliver medical fluid to a patient. Such an apparatus, and in particular an administration feeding set, is disclosed in the above-referenced U.S. Pat. No. 7,462,170. As shown in FIGS. 5A and 5B, the flow control apparatus 40 generally comprises a valve controller 42 (FIG. 5B) for actuating the valve rotor 34 and a peristaltic pump 44 for manipulating the tubing 18 to move fluid through the medical fluid delivery set 10. Upon initiation of a medical fluid delivery session, the valve controller 42 and the peristaltic pump 44 operate automatically to deliver the medical fluid to the patient.

At certain times, the delivery set 10 requires maintenance. For example, the tubing 14, 16, 18 may become clogged during delivery of a medical fluid and require flushing. Additionally, at the completion of a medical fluid delivery session, the delivery set 10 may need to be cleaned. The manual valve actuator 12 can be used to manually conduct these maintenance procedures, in addition to other functions.

Referring to FIGS. 6-13, the manual valve actuator 12 comprises a holder 50 for holding the valve mechanism 24, a valve driver 52 adapted for operative engagement with the rotor of the valve mechanism, and a handle 54 for manually rotating the valve driver. As will be described, the handle and valve driver 52 are rotatable as a unit relative to the holder 50 about an axis A-A. This rotation causes rotation of the rotor 34 of the valve mechanism 24 when the mechanism is received in the holder 50.

Figure 6:
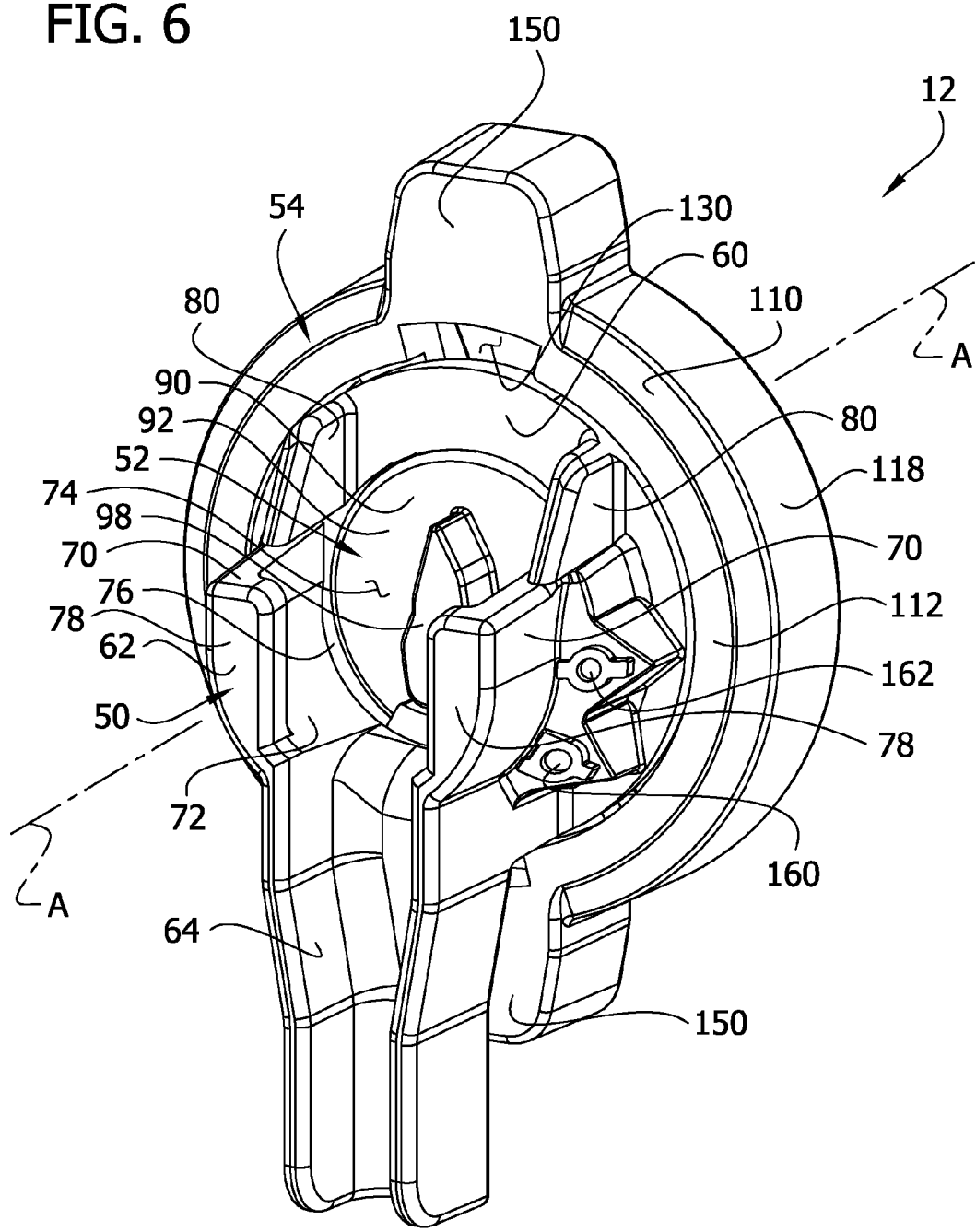
FIG. 6 is an enlarged front perspective of the manual valve actuator of FIG. 1.
Figure 7:
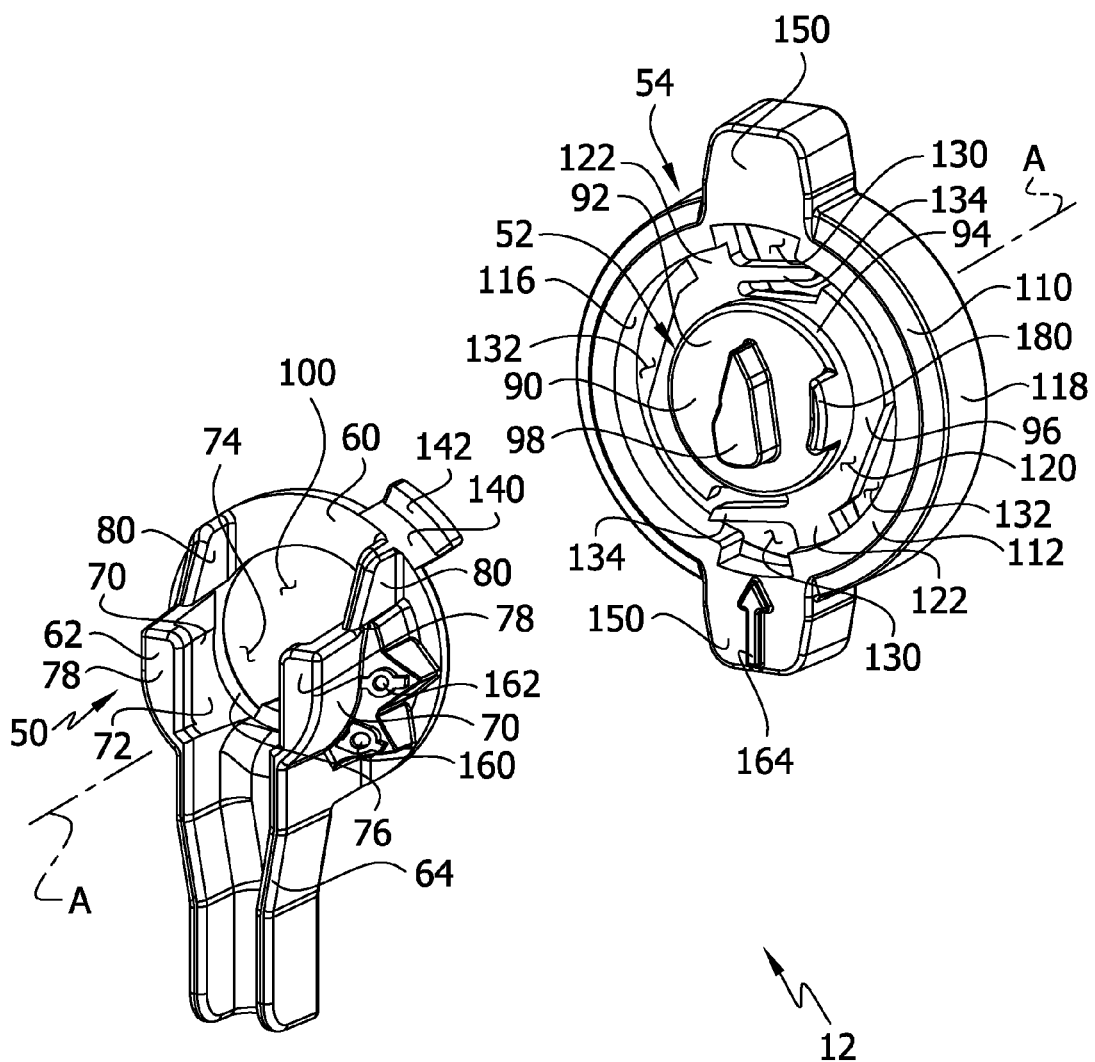
FIG. 7 is an exploded front perspective of the manual valve actuator.
Figure 8:
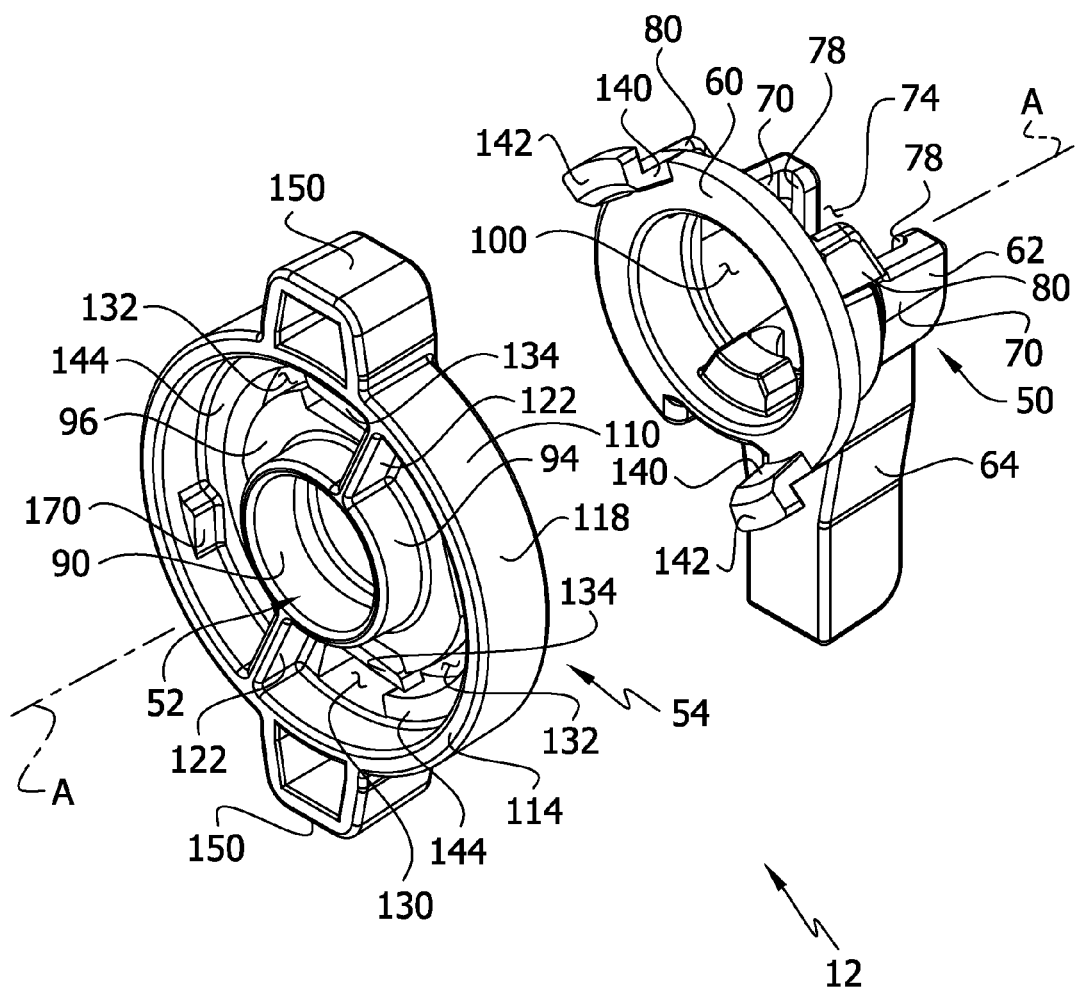
FIG. 8 is an exploded rear perspective of the manual valve actuator.
Figure 9:
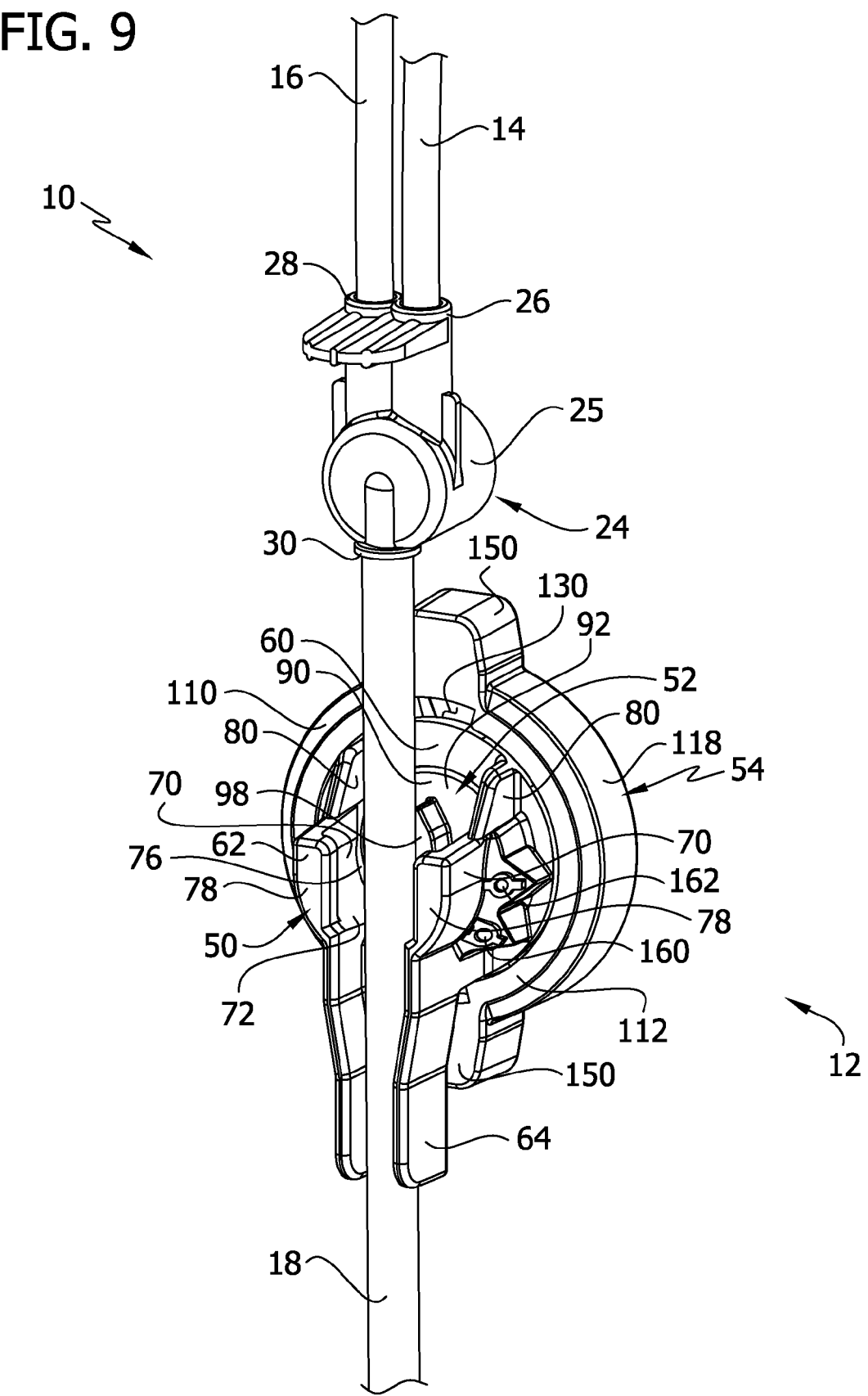
FIG. 9 is a view similar to FIG. 1 but showing the medical fluid delivery set partially loaded.

As shown in FIGS. 6-8, the holder 50 comprises a ring 60 centered on axis A-A, a pocket 62 affixed to the front of the ring, and a channel 64 extending down from the pocket. In one embodiment, these parts are integrally formed as one piece in a molding operation, for example.

The pocket 62 of the holder 50 is generally U-shaped, having two opposing sides 70, a base 72, and an open end 74 opposite the base. The back of the pocket 62 is partially closed by an inner edge margin 76 of the ring 60, and the front of the pocket is partially closed by a pair of lips 78 extending from the sides of the pocket at a location spaced from the back of the pocket. The pocket 62 is configured such that valve housing 25 of the valve mechanism 24 can be slidably moved into the pocket through the open end 74 of the pocket to a position in which the valve mechanism is received snugly between the sides 70 of the pocket and also snugly between the inner edge margin 76 of the ring 60 and the lips 78. A pair of spaced-apart guides 80 project upward from opposite sides 70 of the pocket 62 to guide the valve housing 25 of the valve mechanism 24 into the pocket.

The channel 64 of the holder 50 extends down from the base 72 of the pocket 62 and is configured to removably receive the delivery tube 18 connected to the valve mechanism 24 of the medical fluid delivery set 10. The channel 64 provides support in addition to that provided by the pocket 62 to hold the valve mechanism 24 against rotation with respect to the holder 50.

The holder 50 can have other configurations without departing from the scope of this invention.

Referring to FIG. 7, the valve driver 52 comprises a circular hub 90 centered on the axis A-A. The hub 90 has a front wall 92, an annular side wall 94, and a radial flange 96 extending circumferentially around the hub at a location spaced rearward of the front wall of the hub. The driver 52 also includes a key 98 projecting forward from the front wall 92 of the hub 90. When the valve driver 52 and holder 50 are assembled (FIG. 6), the ring 60 of the holder is positioned flat against the flange 96 on the hub 90, with the front of the hub received in a central opening 100 of the ring and the key 98 projecting forward into the pocket 62 of the holder. The key 98 is sized and shaped for reception in the channel 36 (or other recess) in the rotor 34 of the valve mechanism 24. The hub 90 is sized to fit closely within the central opening 100 of the ring 60 but not so tightly as to inhibit rotational movement of the hub and valve driver 52 relative to the holder 50.

Referring to FIGS. 7 and 8, the handle 54 comprises an annular body 110 having a front rim 112, a back rim 114, an interior circumferential surface 116, and an exterior circumferential surface 118. The interior surface 116 defines a central opening 120 in the body 110 having a central axis coincident with axis A-A. The valve driver 52 is centered in the opening 120 of the annular body 110 and is connected to the body by a pair of radial supports 122 bridging between the side wall 94 of the hub 70 and the interior surface 116 of the annular body 110. As a result, the hub 90 and annular body 110 rotate as a unit. The hub 90 of the valve driver 52 is set back from the front rim 112 of the handle body 110 so that when the holder 50, handle 54 and valve driver 52 are assembled, the ring 60 of the holder 50 is received in the central opening 120 of the handle body and the hub is received in the central opening 100 of the ring 60, as previously described. The fit of the ring 60 in the central opening 120 of the handle body 110 is relatively snug to maintain the ring centered in the opening on axis A-A. The handle 54 and valve driver 52 are desirably formed as a one-piece unit (e.g., a one-piece molded part), but they can be formed as separate parts.

As best illustrated in FIG. 7, the annular body 110 and radial flange 96 of the hub 90 are configured to provide a pair of diametrically opposite openings 130, a pair of arcuate slots 132 extending from respective openings, and a pair of flexibly resilient arms 134 located adjacent respective openings 130. In their relaxed state, these arms 134 block entry into respective slots 132. The purpose of the openings 130, slots 132 and resilient arms 134 will become apparent.

Referring again to FIG. 7, the holder 50 is held in assembly with the handle 54 and valve driver 52 by diametrically opposite legs 140 that extend rearward from the perimeter of the holder ring 60. Each leg 140 has a foot 142 that extends generally radially outward with respect to the center of the holder ring 60. To install the holder 50 on the handle/valve driver unit 54, 52, the feet 142 on the legs 140 are passed through the openings 130 of the unit to position the ring 60 of the holder flat against the radial flange 96. The handle/valve driver unit 54, 52 is then rotated to move the legs 140 into respective slots 132. The resilient arms 134 deflect to permit entry of the legs 140 into the slots 132 after which they spring back to block rotational removal of the legs from the slots. The legs 140 are held against removal from the slots 132 in an axial direction by the feet 142 which are positioned for engagement with rearward-facing internal radial shoulders 144 on the annular body 110 (see FIG. 8). Thus, the holder 50 is held in assembly with the handle/valve driver unit 54, 52 while permitting the unit to be rotated to various angular positions relative to the holder, as will be described. The legs 140 on the holder 50 move in respective arcuate slots 132 during such rotation.

The valve driver 52 and handle 54 can have other configurations within the scope of this invention.

The handle 54 is rotatable to move the valve driver 52 between a loading position and one or more selected fluid-flow positions. In the loading position, illustrated in FIG. 9, the key 98 on the valve driver 52 is positioned to allow the valve mechanism 24 to be loaded into the pocket 62, i.e., moved into a position in which the valve mechanism is fully seated in the pocket and the key is received in the channel 36 (or other recess) of the rotor 34. Further, the arrangement is such that the rotor 34 must be in a no-flow position before the valve mechanism 24 can be loaded into the pocket 62. To facilitate rotation of the handle 54 and valve driver 52, one or more tabs 150 project outward in a radial direction from the annular body 110 of the handle 54. In the illustrated embodiment, two such tabs 150 are provided at diametrically opposite locations on the handle 54. When the manual valve actuator 12 is in its loading position, the tabs 150 are desirably aligned with the longitudinal axis of the pocket 62 and channel 64, i.e., an axis extending through the open end 74 and base 72 of the pocket and along the length of the channel 64.

Referring to FIG. 6, the holder has two rotational indicators 160, 162 disposed at predetermined circumferential positions along the holder ring 60 to signify rotational positions to which the handle 54 may be rotated to change a fluid flow path through the valve mechanism 24. In the illustrated embodiment, the indicators 160, 162 comprise triangular formations at one side of the pocket 62 pointing toward the perimeter of the ring 60. Each indicator 160, 162 has a different marking, and the markings correspond to different types of medical fluid delivery sets, as described above. The first indicator 160 corresponds to the delivery set 10 having two source tubes 14, 16. This indicator 160 signifies a rotational position, shown in FIG. 10A, to which the handle 54 may be rotated to actuate the valve rotor 34 to permit fluid flow from one of the source tubes 14, 16 through the valve mechanism 24 and the delivery tube 18. The second indicator 162 corresponds to the delivery set 10' having a single source tube 14'. This indicator 162 signifies a rotational position, shown in FIG. 10B, to which the handle 54 may be rotated to permit fluid flow from the single source tube 14' through the valve mechanism 24'. Alternatively, the holder 50 may have only one indicator 160, 162 and be for use with only one type of fluid delivery set (e.g., delivery sets with one or two source tubes). The handle 54 may also have an indicator 164 that assists in aligning the handle 54 with the rotational indicators 160, 162 of the holder 50. In the illustrated embodiment, the handle indicator 164 is in the form of an arrow (also designated 124), which is disposed on the lower tab 150.

Figure 10A:
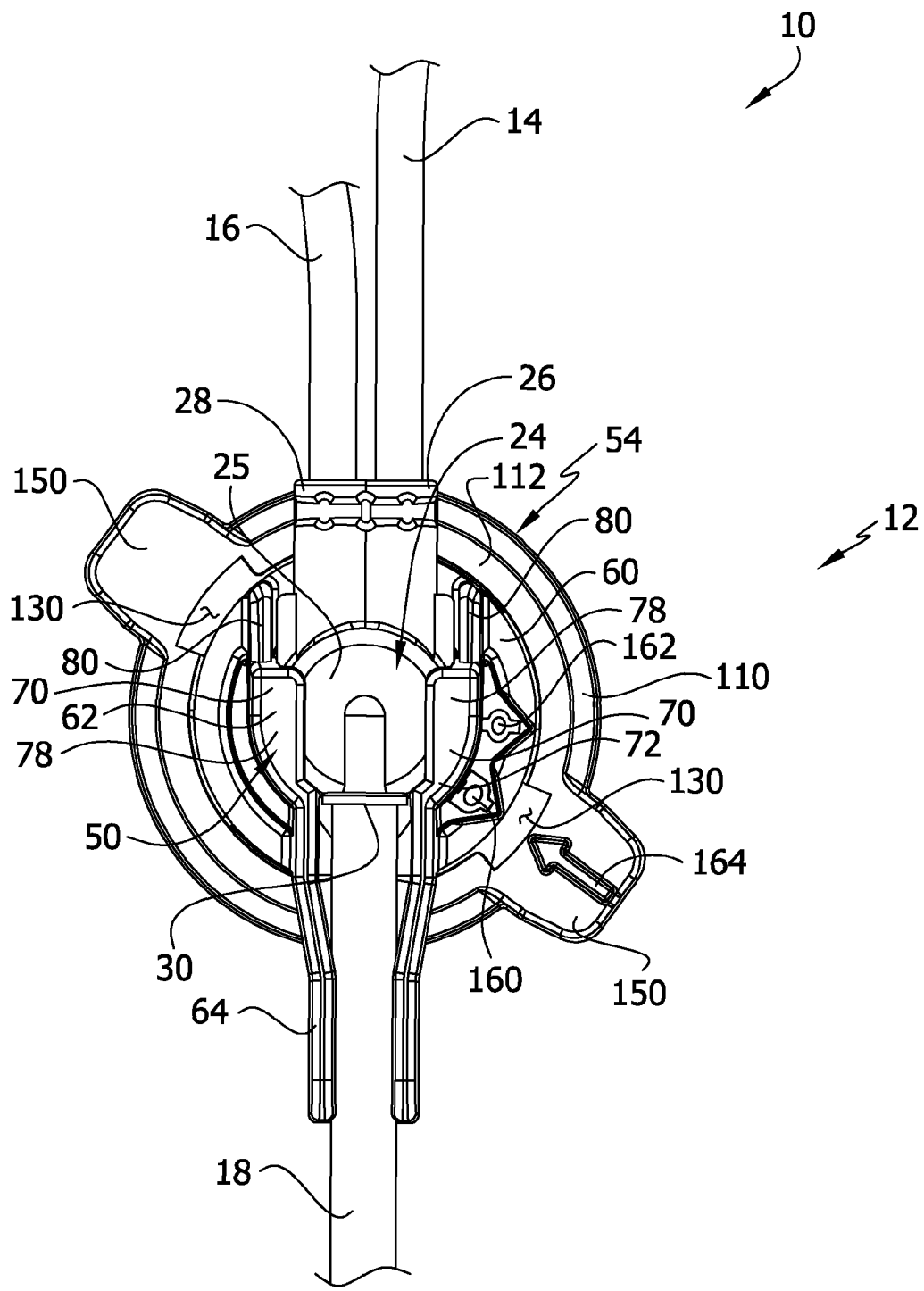
FIG. 10A is a front elevation of the medical fluid delivery set of FIG. 2A loaded on the manual valve actuator, a handle of the manual valve actuator being shown turned to a first position.
Figure 10B:
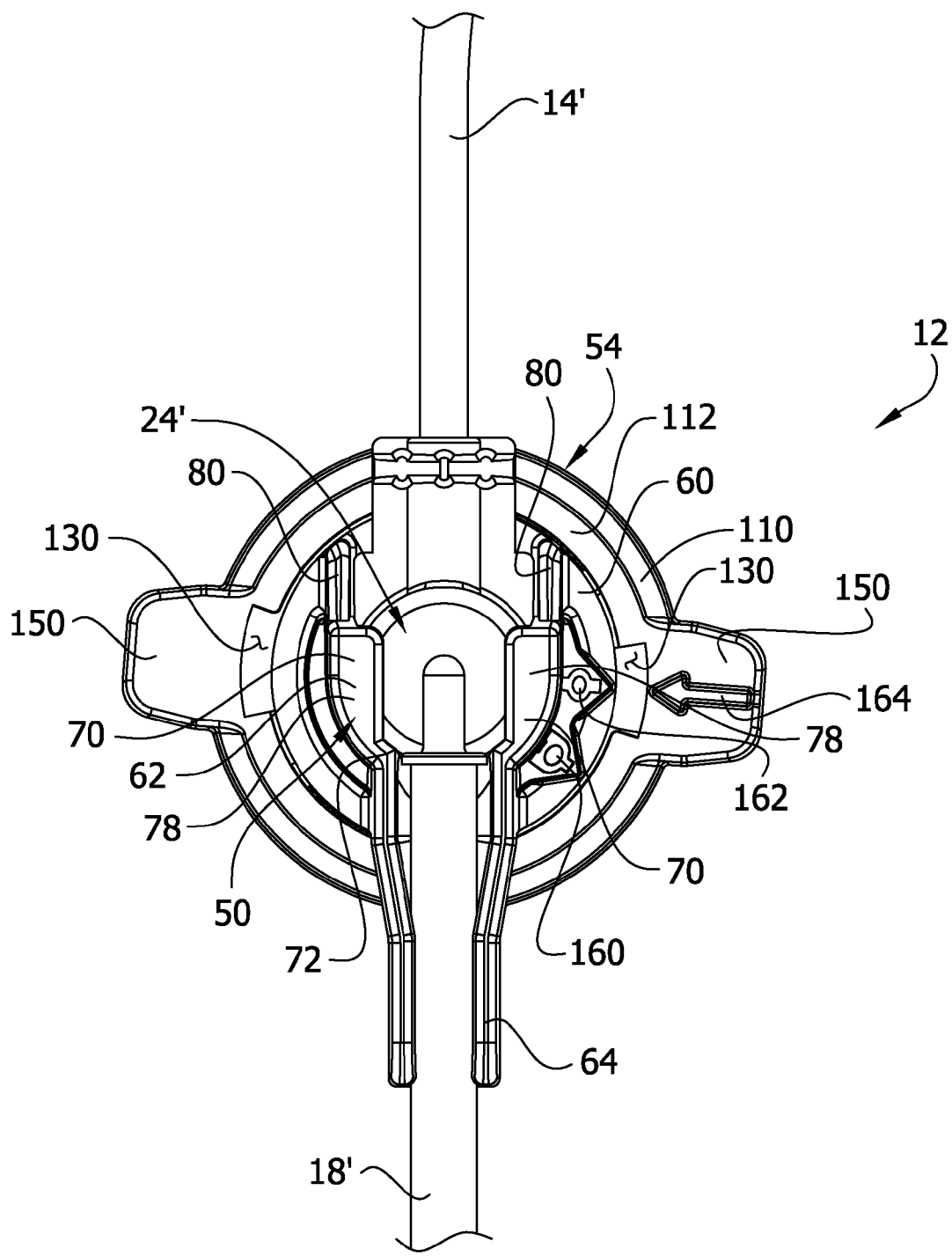
FIG. 10B is a front elevation of the medical fluid delivery set of FIG. 2B loaded on the manual valve actuator, the handle of the manual valve actuator being shown turned to a second position.
Figure 12A:
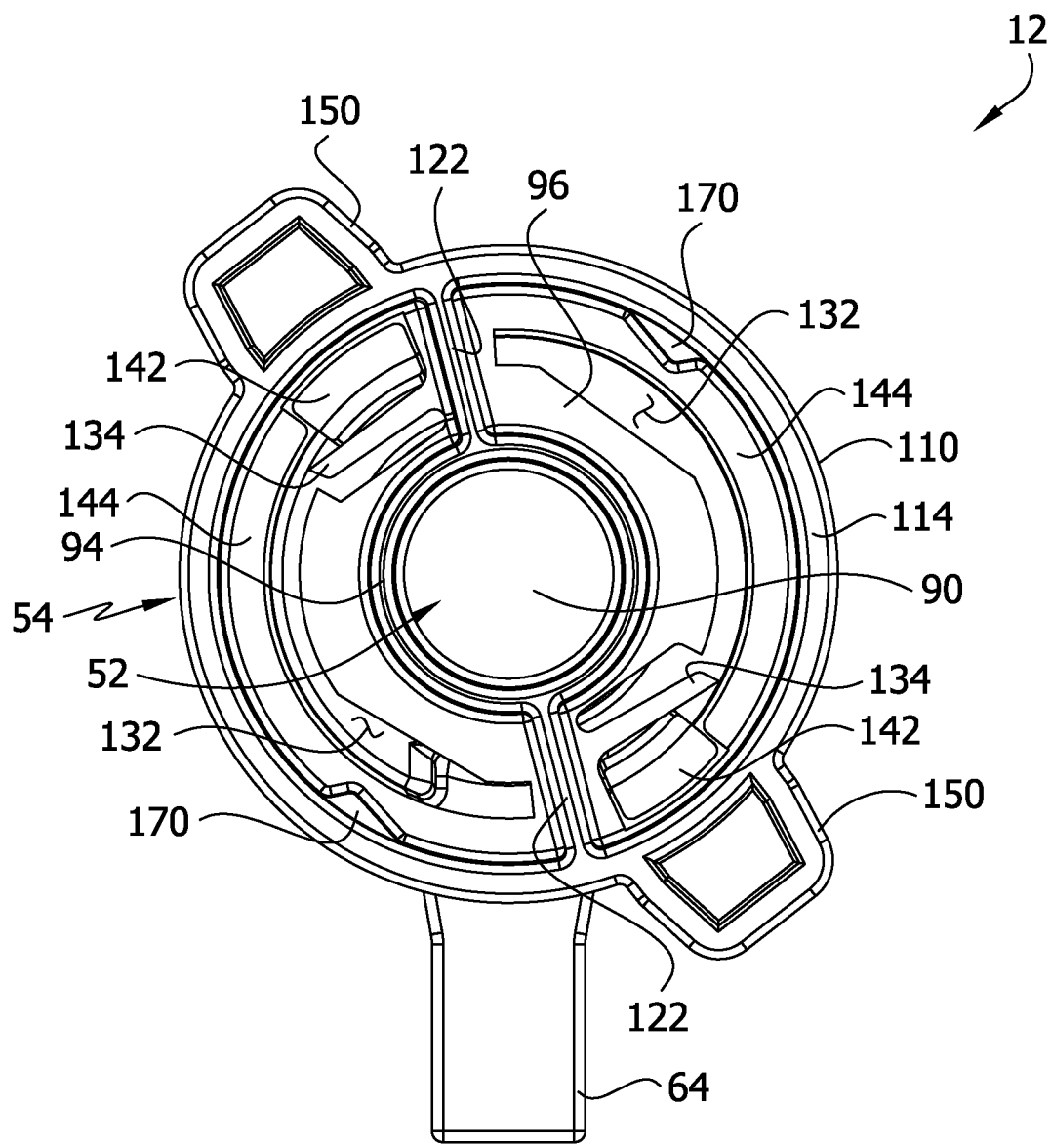
FIG. 12A-12C are rear elevations showing in sequence assembly of a holder and a handle/valve driver unit to form the manual valve actuator.
Figure 12B:
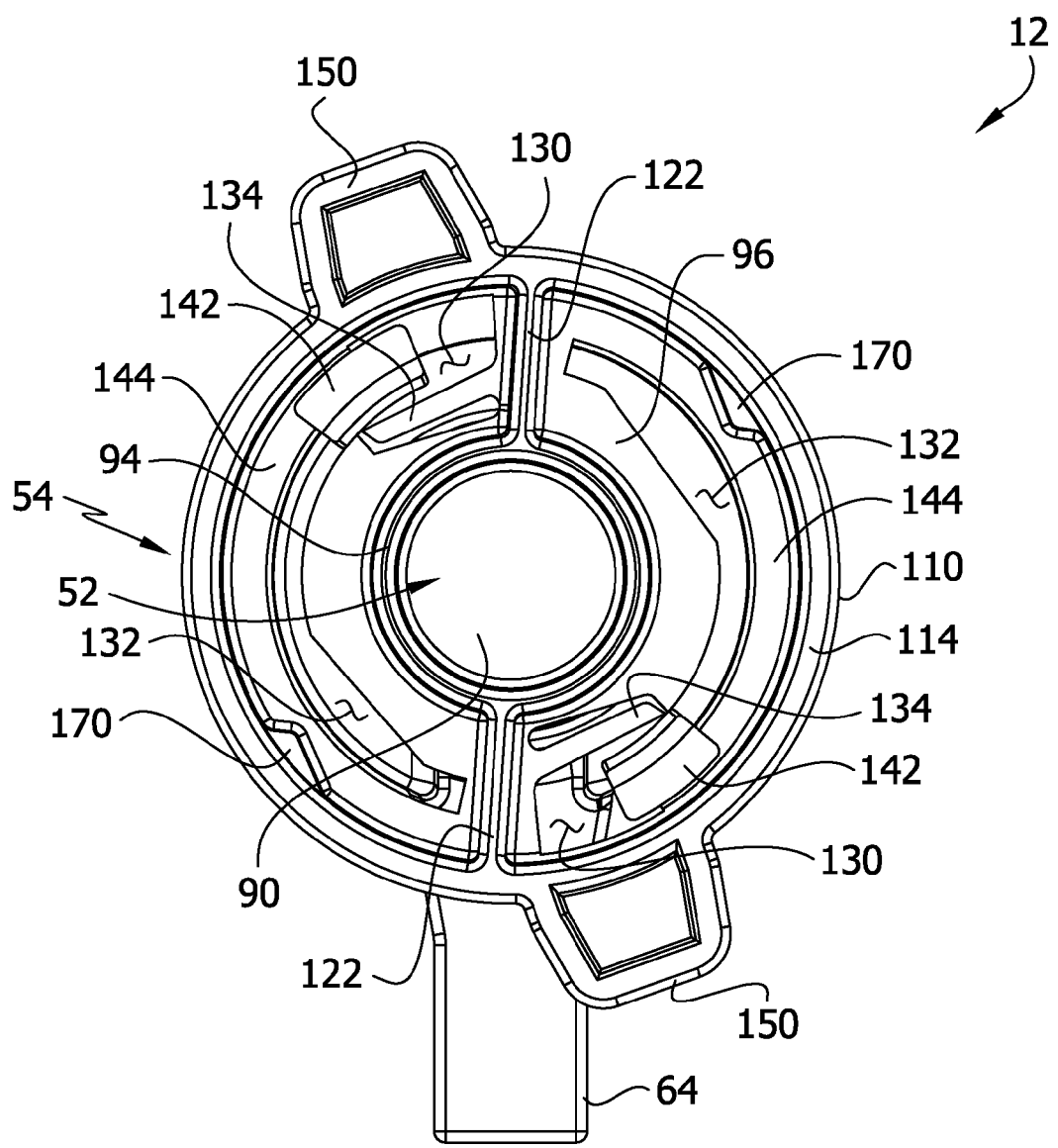
Figure 12C:
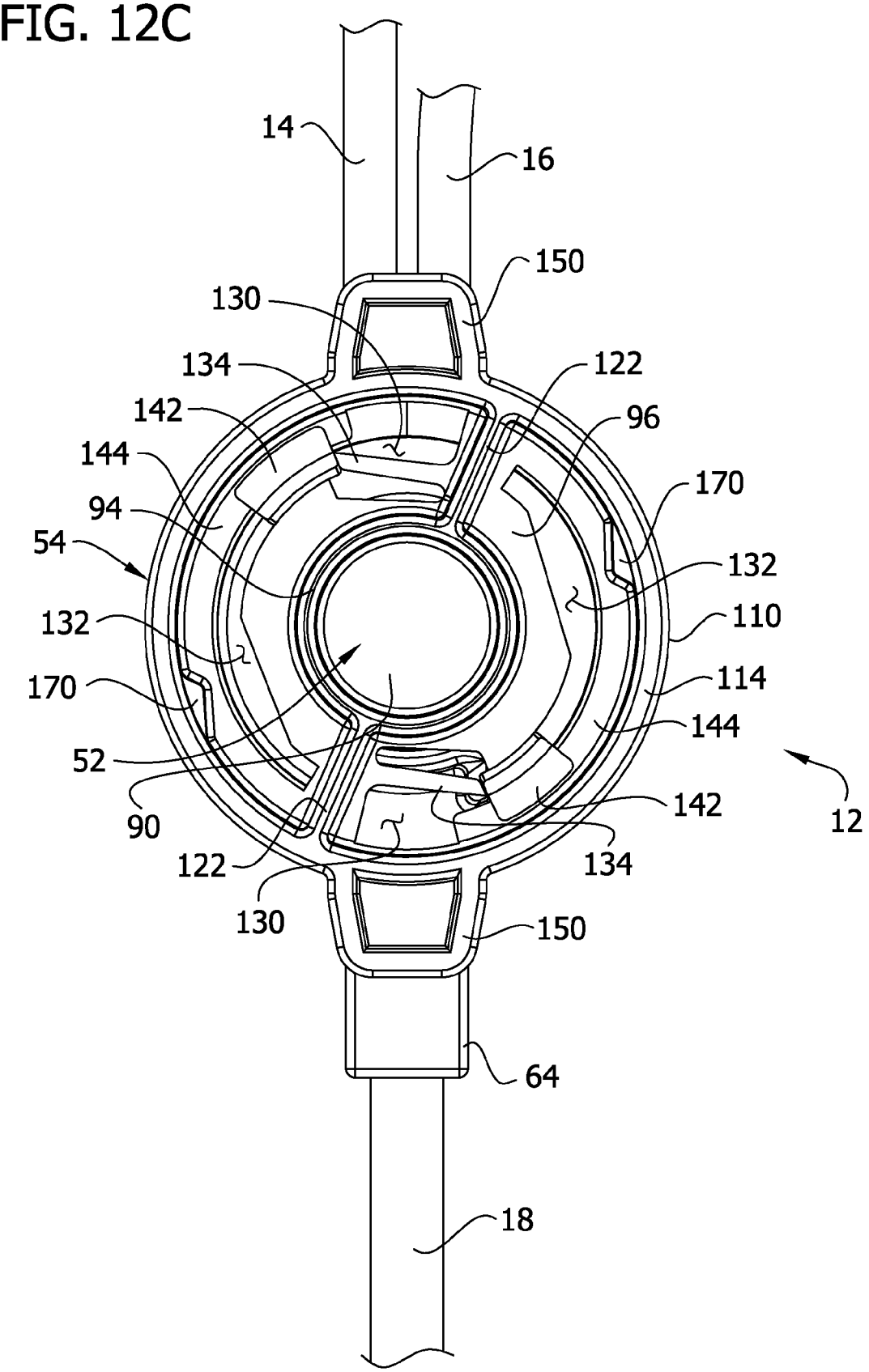
Figure 13A:
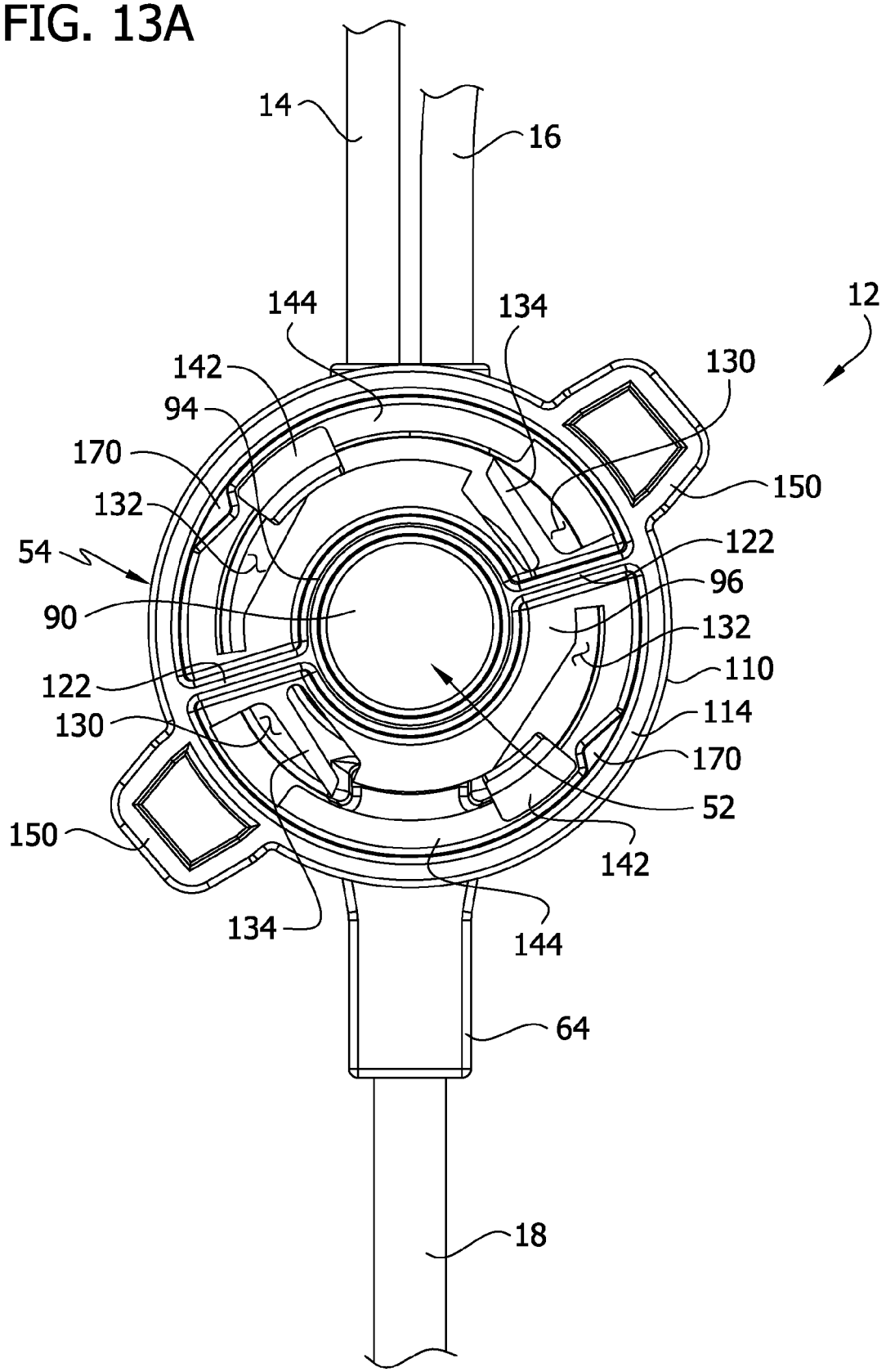
FIG. 13A is a rear elevation of the manual valve actuator and the medical fluid delivery set of FIG. 10A.
Figure 13C:
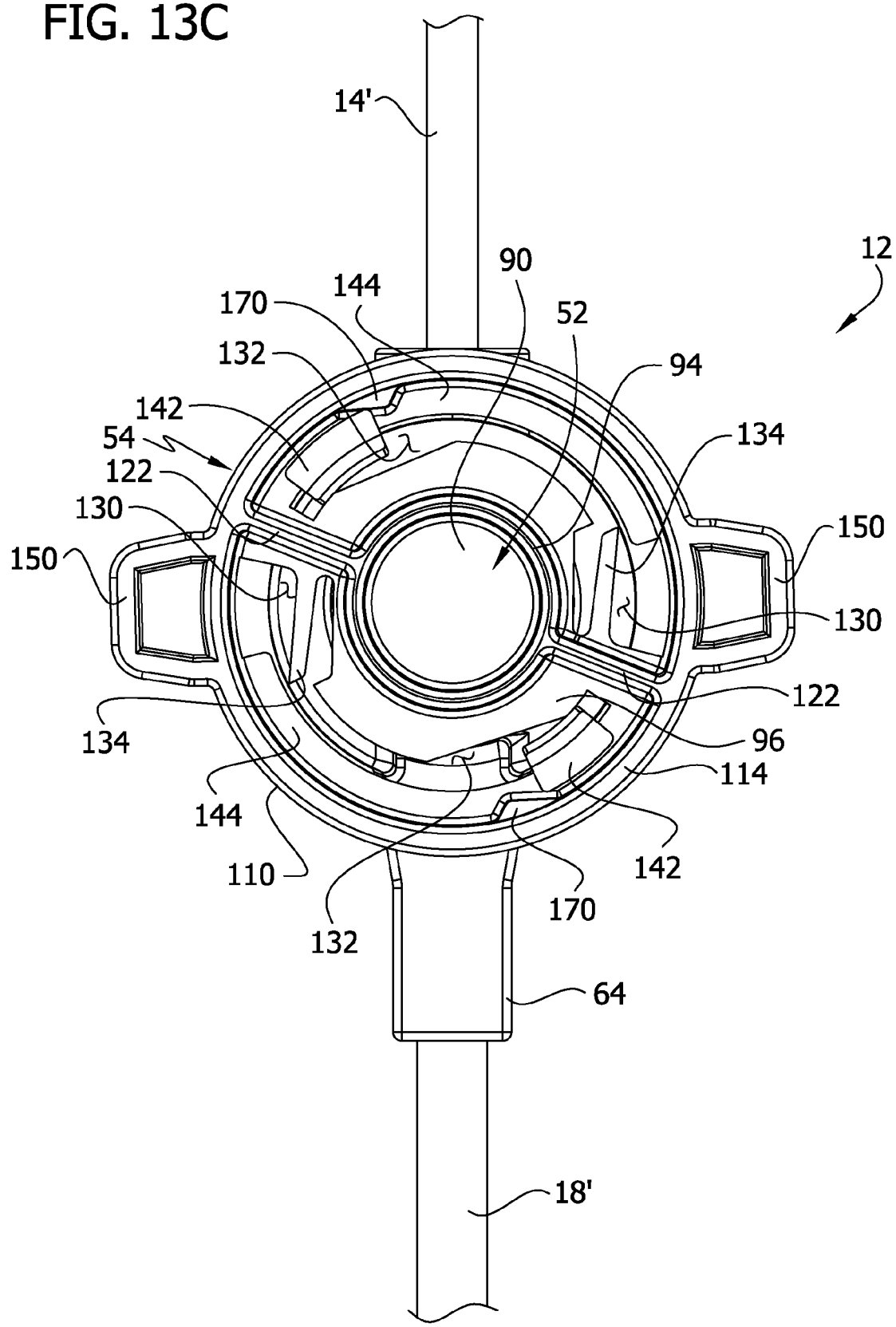
FIG. 13C is a view similar to FIG. 13B but showing the handle of the manual valve actuator turned to the position shown in FIG. 10B.

Two detents 170 provide additional resistance against rotation of the handle 54 from a position in which the handle arrow 164 is aligned with the first indicator 160 on the holder 50 to a position in which the handle arrow is aligned with the second indicator 162 on the holder. As shown in FIGS. 8, 12 and 13, the detents 170 are formed on the interior surface 116 of the annular body 110 of the handle 54 at locations rearward of the internal shoulders 144. The detents 130 create rotational resistance by interfering with the path of the legs 140 as they move in the slots 132. The feet 142 on the legs 140 engage a first side of respective detents 170 when the handle 54 is turned to a rotational position in which the handle arrow 164 is aligned with the first indicator 160 on the holder 50, as shown in FIGS. 10A and 13A. Rotation of the handle 54 toward the positions shown in FIGS. 10B and 13B causes the legs 140 to deflect radially inward as the feet 142 of the legs engage the detents 170. The width of the slots 132 is increased to provide clearance for the legs 140 at the point of maximum inward deflection, as shown in FIG. 13B. Once the legs 140 have been rotated beyond the detents 170, as shown in FIG. 13C, the legs spring back to their original radial positions. In this rotational position, the arrow 164 on the handle 54 is aligned with the second indicator 162 on the holder 50, as shown in FIG. 10B. Also, as shown in FIG. 13C, each detent 170 is spaced from the closed end of a respective slot 132 a distance only slightly greater than the width dimension of a leg 140 on the holder 50 so that the handle/valve driver unit 54, 52 is held substantially stationary until the handle is forcibly rotated to a different position.

Figure 11:
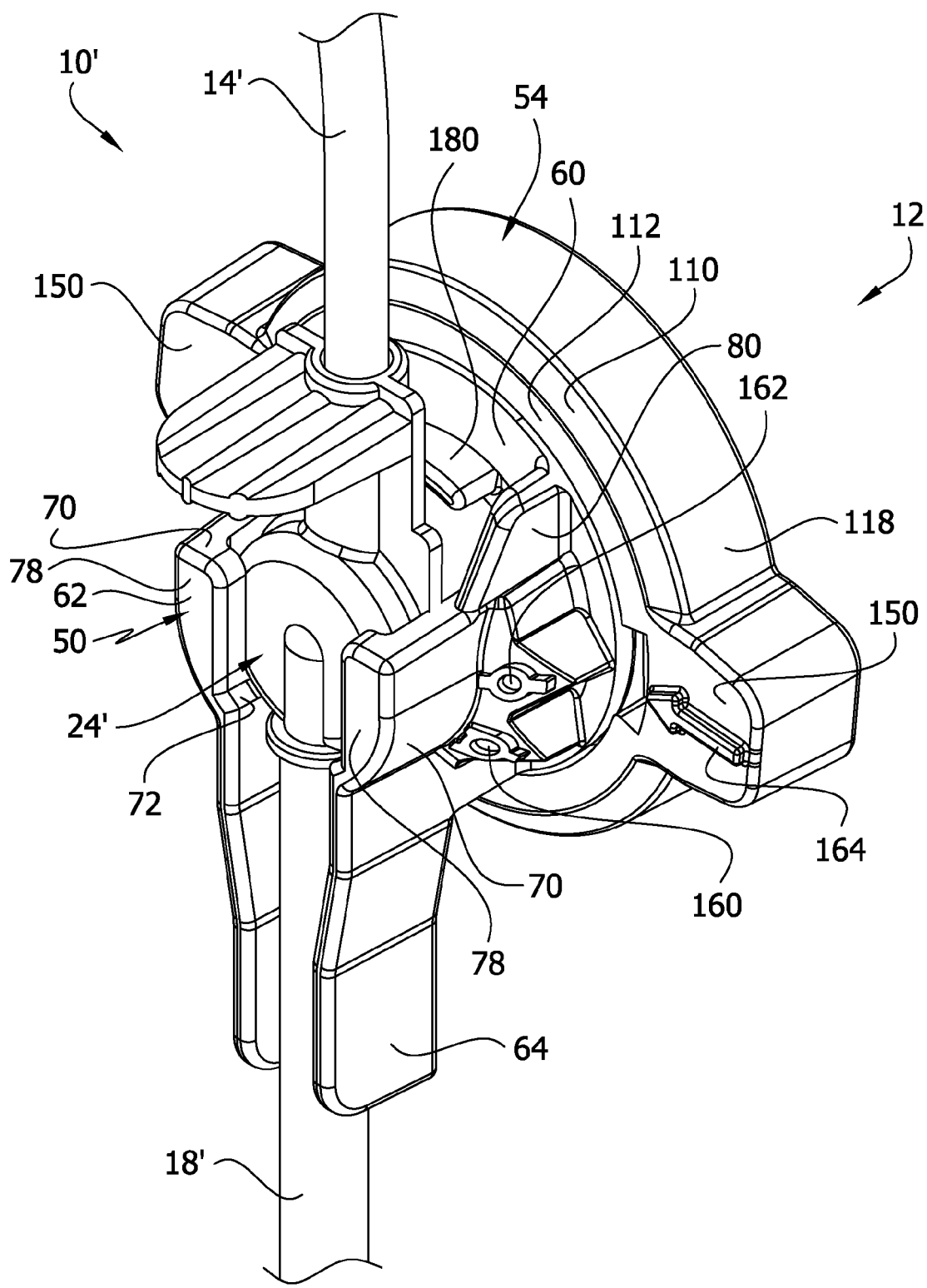
FIG. 11 is a front perspective of the medical fluid delivery set and manual valve actuator as shown in FIG. 10B.

A lock 180 extends forward from the front wall of the hub 90 of the valve driver 52 and is adapted to engage the valve mechanism 24 to prevent removal of the valve mechanism from the holder 50 whenever the valve rotor 34 is in a rotational position permitting fluid flow through the valve mechanism. As shown in FIG. 7, the lock 180 is disposed at the right side of the valve driver 52 in an unlocked position when the manual valve actuator 12 is in its loading position, i.e., the position in which the valve rotor 34 of a loaded valve mechanism 24 prevents fluid flow through the valve mechanism. Rotation of the valve driver 52 via the handle 54 in a counterclockwise direction also causes rotation of the lock 180 in a counterclockwise direction. Thus, as the valve driver 52 turns the valve rotor 34, the lock 180 rotates to a position overlying the open end 74 of the U-shaped pocket 62, thereby blocking sliding removal of the valve mechanism 24 from the pocket. When the handle 54 is turned to a rotational position in which the arrow 164 on the handle is aligned with the first indicator 160 on the holder 50, the lock 180 partially blocks the open end 74 of the U-shaped pocket 62. When the handle 54 is turned to a rotational position in which the arrow 164 on the handle is aligned with the second indicator 162 on the holder 50, the lock 180 fully blocks the open end 74 of the U-shaped pocket 62, as shown in FIG. 11.

In use, the handle 54 of the manual valve actuator 12 is first moved to the stated loading position (FIGS. 6 and 9) in which the lock 180 on the valve driver 52 is clear of the open end 74 of the pocket 62 of the holder 50. The valve mechanism 24 of the medical fluid delivery set 10 is then inserted into the pocket 62 to a position in which the key 98 of the valve driver 52 is received in the channel recess 36 in the rotor 34 of the mechanism (FIG. 1). The delivery tube 18 of the fluid delivery set 10 extending down from the valve mechanism 24 is placed in the channel 64 of the holder 50.

Once the valve mechanism 24 is loaded on the manual valve actuator 12, the handle 54 is turned using the tabs 150 to rotate the valve driver 52 and thereby the valve rotor 34 to a position permitting fluid flow though the medical fluid delivery set 10. If a medical fluid delivery set 10 having two source tubes 14, 16 is loaded on the manual valve actuator 12, the handle 54 is turned such that the arrow 164 on the handle 54 is aligned with the first indicator 160 on the holder 50. Such rotation turns the valve rotor 34 to a position permitting fluid flow from one of the source tubes 14, 16 (desirably the source tube 16 in fluid communication with the rinsing fluid source 22) through the valve mechanism 24 and the delivery tube 18. When the handle 54 is turned to this rotational position, the lock 180 partially blocks the valve mechanism 24 from removal from the pocket 62, and the detents 170 provide resistance against further rotation of the handle in a counterclockwise direction. If a medical fluid delivery set 10' having a single source tube 14' is loaded on the manual valve actuator 12, the handle 54 is turned against and beyond the resistance of the detents 170 until the arrow 164 on the handle 54 is aligned with the second indicator 162 on the holder 50. In this rotational position, fluid flow is permitted from the single source tube 14' through the valve mechanism 24' and the delivery tube 18', and the lock 180 fully blocks the valve mechanism from removal from the pocket 62.

A rinsing fluid from the rinsing fluid source 22 may then be flushed through the medical fluid delivery set 10, 10'. To move the rinsing fluid through the delivery set 10, a user may manually squeeze the rinsing fluid source 22 or otherwise apply pressure to the rinsing fluid. The pressure on the rinsing fluid forces it through the source tube 16, the valve mechanism 24, and finally the delivery tube 18. The user may apply sufficient force to the rinsing fluid source 22 to unclog any blockage in the tubing 18 and clean the tubing of any medical fluid.

After the medical fluid delivery set 10 has been cleaned, pressure is relieved from the rinsing fluid source 22, and the handle 54 is rotated in a clockwise direction back to its original or loading position. Rotation of the handle 54 in this direction moves the lock 180 to its original unlocked position and turns the valve rotor 34 to its closed position, preventing fluid flow through the delivery set 10. The valve mechanism 24 may then be removed from the manual valve actuator 12.

Alternatively, the delivery set 10 may be cleaned using the flow control apparatus 40. However, this procedure has significant disadvantages compared to using the manual valve actuator 12. The flow control apparatus 40 moves fluid through the delivery set 10 with the peristaltic pump 44. The pump 44 generates a flushing pressure that is substantially lower than the pressure that can be achieved manually. The flow control apparatus 40 may not achieve a pressure high enough to successfully flush clogged tubing. Additionally, the peristaltic pump 44 operates at a relatively slow rate. Therefore, flushing rinsing fluid through the delivery set 10 takes a significant amount of time. For these and other reasons, it is advantageous to use the manual valve actuator 12 for cleaning and performing other functions with the medical fluid delivery set 10.

Components of the manual valve actuator 12 as described above may comprise different shapes or be assembled in a different configuration and still be within the scope of the present invention. For example, the manual valve actuator 12 may have a different construction to conform to a different type of valve mechanism 24. The manual valve actuator 12 may be configured to actuate a valve mechanism 24 by sliding movement of the handle 54 rather than rotational movement. Such a manual valve actuator 12 would be constructed to suitably hold the valve mechanism 24 and enable manual actuation of the valve.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawing shall be interpreted as illustrative and not in a limiting sense.

What is claimed is:

1. A manual valve actuator for a medical fluid delivery set including a valve mechanism having a valve rotor capable of regulating a flow of fluid delivered from a pump through the valve mechanism, the manual valve actuator comprising:
   a holder adapted to removably receive the valve mechanism therein such that removal of the valve mechanism from the holder does not prevent the valve mechanism from regulating fluid flow through the valve mechanism, the holder being shaped to hold the valve mechanism against rotation with respect to the holder;

a valve driver mounted for rotation with respect to the holder about an axis of rotation, the valve driver projecting into the holder to operatively engage the valve rotor when the valve mechanism is received in the holder;

a handle operatively connected to the valve driver for rotating the valve driver and thereby the valve rotor when the valve mechanism is received in the holder; and a lock positioned with respect to the holder to engage the valve mechanism to prevent removal of the valve mechanism from the holder whenever the valve rotor is in a rotational position permitting fluid flow through the valve mechanism, the lock being moveable to a position to permit removal of the valve mechanism from the holder when the valve rotor is in a rotational position preventing fluid flow through the valve mechanism.

2. A manual valve actuator according to claim 1 wherein the holder comprises a ring and a pocket connected to the ring adapted to removably receive the valve mechanism, the pocket having an open top positioned to receive the valve mechanism into the pocket passing in a direction perpendicular to the axis of rotation of the valve driver, wherein the holder is separate from the pump.

3. A manual valve actuator according to claim 2 wherein the holder further comprises a channel extending from the pocket adapted to removably receive a tube of the medical fluid delivery set connected to the valve mechanism.

4. A manual valve actuator according to claim 2 wherein the valve driver is rotatably disposed within a central opening of the ring.

5. A manual valve actuator according to claim 4 wherein the valve driver is sized and shaped for reception into a recess defined by the valve rotor for engaging the valve rotor.

6. A manual valve actuator according to claim 4 wherein the handle is annular and has a central opening, the ring being disposed within the central opening.

7. A manual valve actuator according to claim 6 wherein the handle and valve driver are connected for conjoint rotation, and wherein the holder has at least one rotational indicator disposed at a predetermined circumferential position along the ring to signify a rotational position at which the handle and valve driver may be rotated to change a fluid flow path through the valve mechanism.

8. A manual valve actuator according to claim 7 wherein the handle has an indicator for alignment with the rotational indicator of the holder.

9. A manual valve actuator according to claim 8 wherein the outer edge of the handle has at least one tab projecting from a periphery of the handle adapted for engaging by a hand of a user and for facilitating rotation of the handle and valve driver.

10. A manual valve actuator as set forth in claim 1 wherein the valve driver is constructed to engage the valve rotor for use in driving rotation of the valve rotor by radial movement of the valve driver with respect to an axis of rotation of the valve rotor.

11. A manual valve actuator according to claim 1 further comprising a detent positioned with respect to the holder such that the detent provides resistance against movement of the handle from a first rotational position to a second rotational position.

12. A manual valve actuator according to claim 1 in combination with a medical fluid delivery set, the medical fluid delivery set comprising:

tubing adapted for fluid flow therethrough, the valve mechanism in fluid communication with the tubing, the valve rotor of the valve mechanism adapted to engage a flow control apparatus for manipulation of the valve mechanism by the flow control apparatus.

13. A manual valve actuator and medical fluid delivery set according to claim 12 wherein the valve mechanism comprises a valve housing having an inlet, an outlet and a chamber, the inlet being in communication with the outlet through the chamber to permit fluid flow through the valve mechanism, and a valve rotor disposed in said chamber, the valve rotor being adapted to operatively engage the valve driver of the manual valve actuator when received in the holder.

14. A manual valve actuator for a medical fluid delivery set including a valve mechanism having a valve rotor capable of regulating a flow of fluid through the valve mechanism, the manual valve actuator comprising:

a holder separate from the valve mechanism and comprising a ring and a pocket connected to the ring adapted to removably receive the valve mechanism such that removal of the valve mechanism from the holder does not prevent the valve mechanism from regulating fluid flow through the valve mechanism, the holder being shaped to hold the valve mechanism against rotation with respect to the holder;

a valve driver rotatably disposed within a central opening of the ring, the valve driver being sized and shaped for reception into a recess defined in the valve rotor, the valve driver projecting into the holder so that the valve driver engages the valve rotor in the recess when the valve mechanism is received in the holder;

a handle operatively connected to the valve driver for rotating the valve driver and thereby the valve rotor when the valve mechanism is received in the holder, the handle being annular with a central opening, the ring of the holder being disposed within the central opening; and a lock positioned with respect to the holder to engage the valve mechanism to prevent removal of the valve mechanism from the holder whenever the valve rotor is in a rotational position permitting fluid flow through the valve mechanism, the lock being moveable to a position to permit removal of the valve mechanism from the holder when the valve rotor is in a rotation position preventing fluid flow through the valve mechanism.

15. A manual valve actuator according to claim 1, wherein the holder comprises a pocket adapted to removably receive the valve mechanism, the pocket having an open top positioned to receive the valve mechanism into the pocket passing through the open top in a direction perpendicular to the axis of rotation of the valve driver.

16. A manual valve actuator according to claim 1, wherein disengagement of the valve mechanism from the valve driver does not prevent the valve mechanism from regulating flow through the valve mechanism.

* * * * *